(12) United States Patent
Hakoshima et al.

(10) Patent No.: US 11,957,411 B2
(45) Date of Patent: Apr. 16, 2024

(54) VISUAL FUNCTION DETECTION APPARATUS, METHOD OF DETECTING VISUAL FUNCTION, AND PROGRAM

(71) Applicant: JVCKENWOOD Corporation, Yokohama (JP)

(72) Inventors: Shuji Hakoshima, Yokohama (JP); Miku Komurata, Yokohama (JP); Katsuyuki Shudo, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 842 days.

(21) Appl. No.: 17/000,455

(22) Filed: Aug. 24, 2020

(65) Prior Publication Data

US 2020/0383568 A1 Dec. 10, 2020

Related U.S. Application Data

(63) Continuation of application No. PCT/JP2019/007120, filed on Feb. 25, 2019.

(30) Foreign Application Priority Data

Mar. 1, 2018 (JP) .................. 2018-036602
Mar. 1, 2018 (JP) .................. 2018-036603

(51) Int. Cl.
*A61B 3/113* (2006.01)
*A61B 3/00* (2006.01)
(Continued)

(52) U.S. Cl.
CPC ............ *A61B 3/113* (2013.01); *A61B 3/0058* (2013.01); *A61B 3/0091* (2013.01);
(Continued)

(58) Field of Classification Search
CPC ..... A61B 3/113; A61B 3/0058; A61B 3/0091; A61B 3/103; A61B 3/0025; G06T 7/0012;
(Continued)

(56) References Cited

U.S. PATENT DOCUMENTS

2014/0320817 A1  10/2014 Kiderman et al.
2017/0007119 A1   1/2017 Cornsweet et al.
2017/0311793 A1  11/2017 Green

FOREIGN PATENT DOCUMENTS

JP        4683280       5/2011
JP     2017-143665      8/2017
(Continued)

OTHER PUBLICATIONS

Examiner provided machine translation of Shudo Katsuyuki, JP 2017158866 A (Year: 2017).*
(Continued)

*Primary Examiner* — Balram T Parbadia
*Assistant Examiner* — Rahman Abdur
(74) *Attorney, Agent, or Firm* — Amin, Turocy & Watson, LLP

(57) ABSTRACT

A visual function detection apparatus includes: a display controller that causes an image for determination to be displayed on a display screen of a display unit; a gazing point detector that detects a position of a gazing point of the test subject observing the display screen; a positional relation detector that detects a positional relation between a position of the image for determination on the display screen and the position of the gazing point; and a visual function detector that detects a visual function of the test subject based on the positional relation.

6 Claims, 26 Drawing Sheets

(51) Int. Cl.
  *G06T 7/00*   (2017.01)
  *G06T 7/70*   (2017.01)
(52) U.S. Cl.
  CPC .............. *G06T 7/0012* (2013.01); *G06T 7/70* (2017.01); *G06T 2207/10012* (2013.01); *G06T 2207/30041* (2013.01)
(58) Field of Classification Search
  CPC ............ G06T 7/70; G06T 2207/10012; G06T 2207/30041
  USPC ........................................................ 351/210
  See application file for complete search history.

(56)                References Cited

FOREIGN PATENT DOCUMENTS

JP      2017-158866     9/2017
WO      2016/116933     7/2016

OTHER PUBLICATIONS

Extended European Search Report for European Patent Application No. 19760204.8 dated May 6, 2021.
International Search Report and Written Opinion for International Application No. PCT/JP2019/007120 dated Apr. 9, 2019, 8 pages.

\* cited by examiner

FIG.14
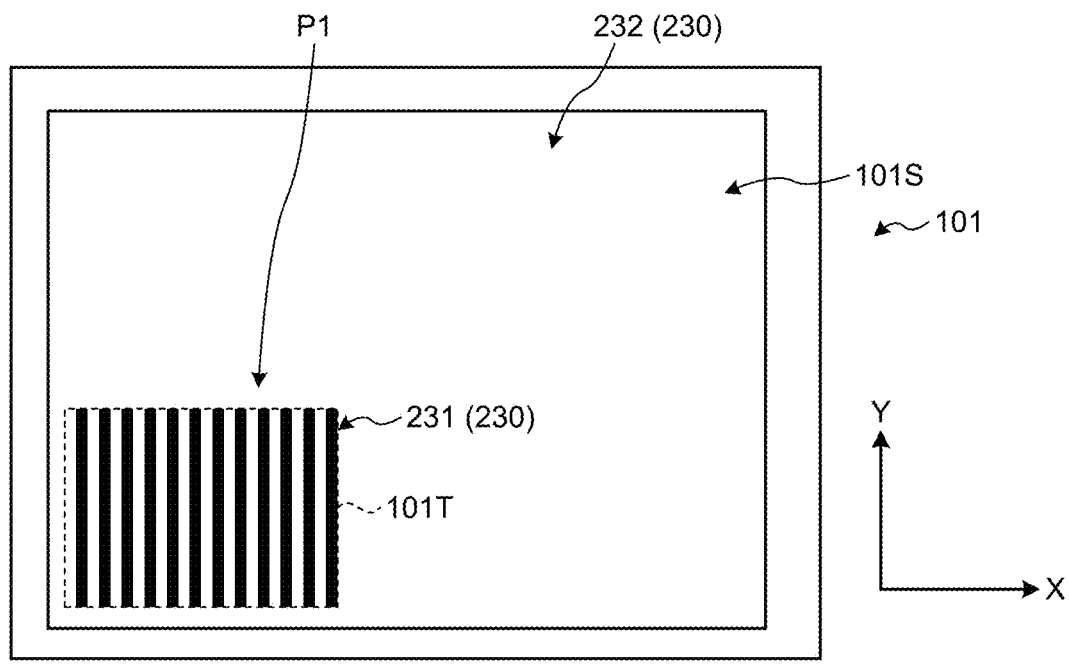
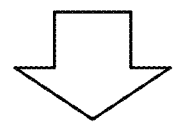
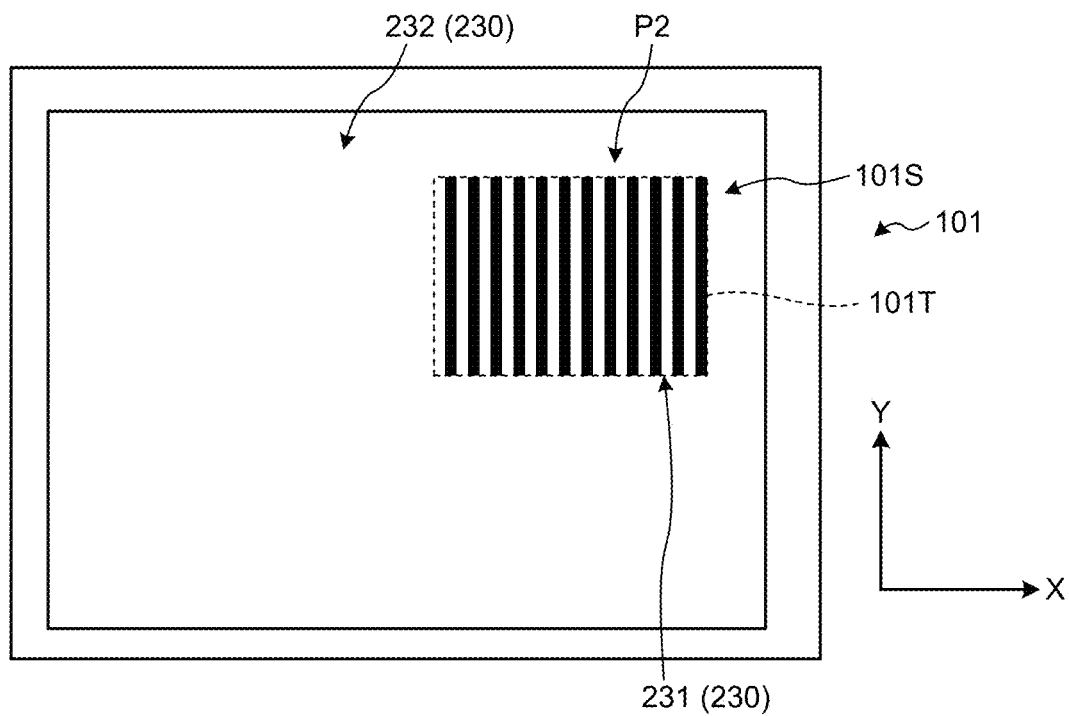

VISUAL FUNCTION DETECTION APPARATUS, METHOD OF DETECTING VISUAL FUNCTION, AND PROGRAM

CROSS-REFERENCE TO RELATED APPLICATIONS

This application is a Continuation of PCT international application Ser. No. PCT/2019/007120 filed on Feb. 25, 2019 which designates the United States, incorporated herein by reference, which claims the benefit of priority from Japanese Patent Application No. 2018-0036602 filed on Mar. 1, 2018 and Japanese Patent Application No. 2018-0036603 filed on Mar. 1, 2018, the entire contents of all of which are incorporated herein by reference.

BACKGROUND

1. Technical Field

The present invention relates to a visual function detection apparatus, a method of detecting a visual function, and a program.

2. Description of the Related Art

Conventionally, there have been methods using Landolt rings for eyesight examinations. Japanese Laid-open Patent Publication No. 2007-143665 (JP-A-2007-143665) discloses a method of displaying Landolt rings on a screen to perform an eyesight examination, for example. Japanese Patent No. 4683280 discloses a method of displaying an image with a striped pattern on a screen and causing an examiner to determine whether a test subject is seeing the image to perform an eyesight examination, for example.

However, in the method of displaying Landolt rings as in JP-A-2007-143665, the test subject is required to self-declare how he/she sees, and an appropriate examination may not be able to be performed depending on the test subject such as an infant. In the case of determining whether the test subject is seeing the image as described in Japanese Patent No. 4683280, objective determination about whether the test subject is actually seeing the image is difficult. Thus, a technique capable of appropriately examining a visual function of the test subject is demanded.

In view of the above problems, an object of the present invention is to provide a visual function detection apparatus, a method of detecting a visual function, and a program capable of appropriately examining the visual function of the test subject.

SUMMARY

According to an aspect, a visual function detection apparatus includes: a display controller configured to cause an image for determination to be displayed on a display screen of a display unit; a gazing point detector configured to detect a position of a gazing point of a test subject observing the display screen; a positional relation detector configured to detect a positional relation between a position of the image for determination on the display screen and the position of the gazing point; and a visual function detector configured to detect a visual function of the test subject based on the positional relation.

According to another aspect, a method of detecting a visual function includes: performing display control to cause an image for determination to be displayed on a display screen of a display unit; performing gazing point detection to detect a position of a gazing point of a test subject observing the display screen; performing positional relation detection to detect a positional relation between a position of a display region of the image for determination on the display screen and the position of the gazing point; and performing visual function detection to detect a visual function of the test subject based on the positional relation.

According to another aspect, a non-transitory computer-readable storage medium storing a program causes a computer to execute a method that includes: display control to cause an image for determination to be displayed on a display screen of a display unit; gazing point detection to detect a position of a gazing point of a test subject observing the display screen; positional relation detection to detect a positional relation between a position of a display region of the image for determination on the display screen and the position of the gazing point; and visual function detection to detect a visual function of the test subject based on the positional relation.

BRIEF DESCRIPTION OF THE DRAWINGS

FIG. 14 is a diagram illustrating a display position of the image for determination.

DETAILED DESCRIPTION

The following describes embodiments of a visual function detection apparatus, a method of detecting a visual function, and a program according to the present invention based on the accompanying drawings. These embodiments do not limit this invention. Components in the following embodiments include ones that can be replaced by those skilled in the art and are easy or substantially the same ones.

In the following description, positional relations among parts will be described by setting a three-dimensional global coordinate system. A direction parallel to a first axis on a certain plane is defined as an X-axial direction, a direction parallel to a second direction on the certain plane orthogonal to the first axis is defined as a Y-axial direction, and a direction parallel to a third axis orthogonal to each of the first axis and the second axis is defined as a Z-axial direction. The certain plane includes an XY plane.

First Embodiment (Visual Function Detection Apparatus)

Figure 1:
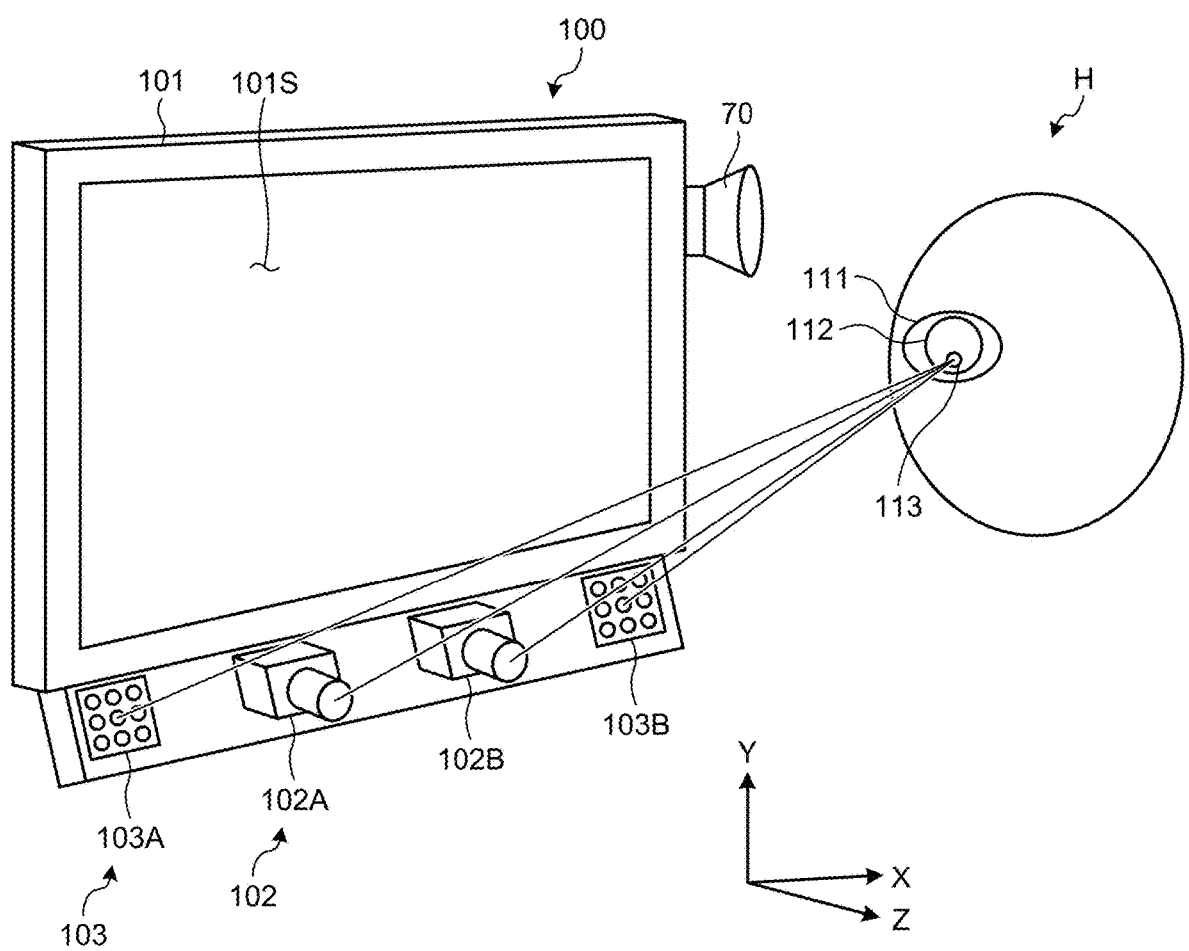
FIG. 1 is a perspective view schematically illustrating an example of a visual function detection apparatus according to an embodiment.

First, the following describes a first embodiment. FIG. 1 is a schematic perspective view of an exemplary visual function detection apparatus according to the present embodiment. The visual function detection apparatus 100 is also used as an evaluation apparatus evaluating a test subject H. As illustrated in FIG. 1, the visual function detection apparatus 100 includes a display apparatus 101, a stereo camera apparatus 102, and an illumination apparatus 103.

The display apparatus 101 as a display unit includes a flat panel display such as a liquid crystal display (LCD) or an organic electroluminescence display (OLED). In the present embodiment, the display apparatus 101 has a display screen 101S. The display screen 101S displays images. The display screen 101S is substantially parallel to the XY plane. The X-axial direction is a right-and-left direction of the display screen 101S, the Y-axial direction is an up-and-down direction of the display screen 101S, and the Z-axial direction is a depth direction orthogonal to the display screen 101S.

The stereo camera apparatus 102 has a first camera 102A and a second camera 102B. The stereo camera apparatus 102 is placed below the display screen 101S of the display apparatus 101. The first camera 102A and the second camera 102B are placed in the X-axial direction. The first camera 102A is placed in a −X direction of the second camera 102B. The first camera 102A and the second camera 102B each include an infrared camera and have an optical system allowing near-infrared light with a wavelength of 850 [nm], for example, to pass and an imaging element that can receive the near-infrared light.

The illumination apparatus 103 has a first light source 103A and a second light source 103B. The illumination apparatus 103 is placed below the display screen 101S of the display apparatus 101. The first light source 103A and the second light source 103B are placed in the X-axial direction. The first light source 103A is placed in a −X direction of the first camera 102A. The second light source 103B is placed in a +X direction of the second camera 102B. The first light source 103A and the second light source 103B each include a light emitting diode (LED) light source and can each emit near-infrared light with a wavelength of 850 [nm], for example. The first light source 103A and the second light source 103B may be placed between the first camera 102A and the second camera 102B.

The illumination apparatus 103 emits near-infrared light as detection light to illuminate an eyeball 111 of the test subject H. The stereo camera apparatus 102 photographs the eyeball 111 with the second camera 102B when the eyeball 111 is irradiated with detection light emitted from the first light source 103A and photographs the eyeball 111 with the first camera 102A when the eyeball 111 is irradiated with detection light emitted from the second light source 103B.

A frame synchronization signal is output from at least either the first camera 102A or the second camera 102B. The first light source 103A and the second light source 103B emit the detection light based on the frame synchronization signal. The first camera 102A acquires image data of the eyeball 111 when the eyeball 111 is irradiated with the detection light emitted from the second light source 103B. The second camera 102B acquires image data of the eyeball 111 when the eyeball 111 is irradiated with the detection light emitted from the first light source 103A.

Upon irradiation of the eyeball 111 with the detection light, part of the detection light is reflected by an iris 112, and the light from the iris 112 enters the stereo camera apparatus 102. Upon irradiation of the eyeball 111 with the detection light, a cornea reflection image 113 as a virtual image of a cornea is formed on the eyeball 111, and the light from the cornea reflection image 113 enters the stereo camera apparatus 102.

Appropriately setting a relative position between the first camera 102A and the second camera 102B and the first light source 103A and the second light source 103B decreases the intensity of the light entering the stereo camera apparatus 102 from the iris 112, while increasing the intensity of the light entering the stereo camera apparatus 102 from the cornea reflection image 113. That is, an image of the iris 112 acquired by the stereo camera apparatus 102 is low in luminance, whereas an image of the cornea reflection image 113 is high in luminance. The stereo camera apparatus 102 can detect a position of the iris 112 and a position of the cornea reflection image 113 based on the luminance of the acquired image.

Figure 2:
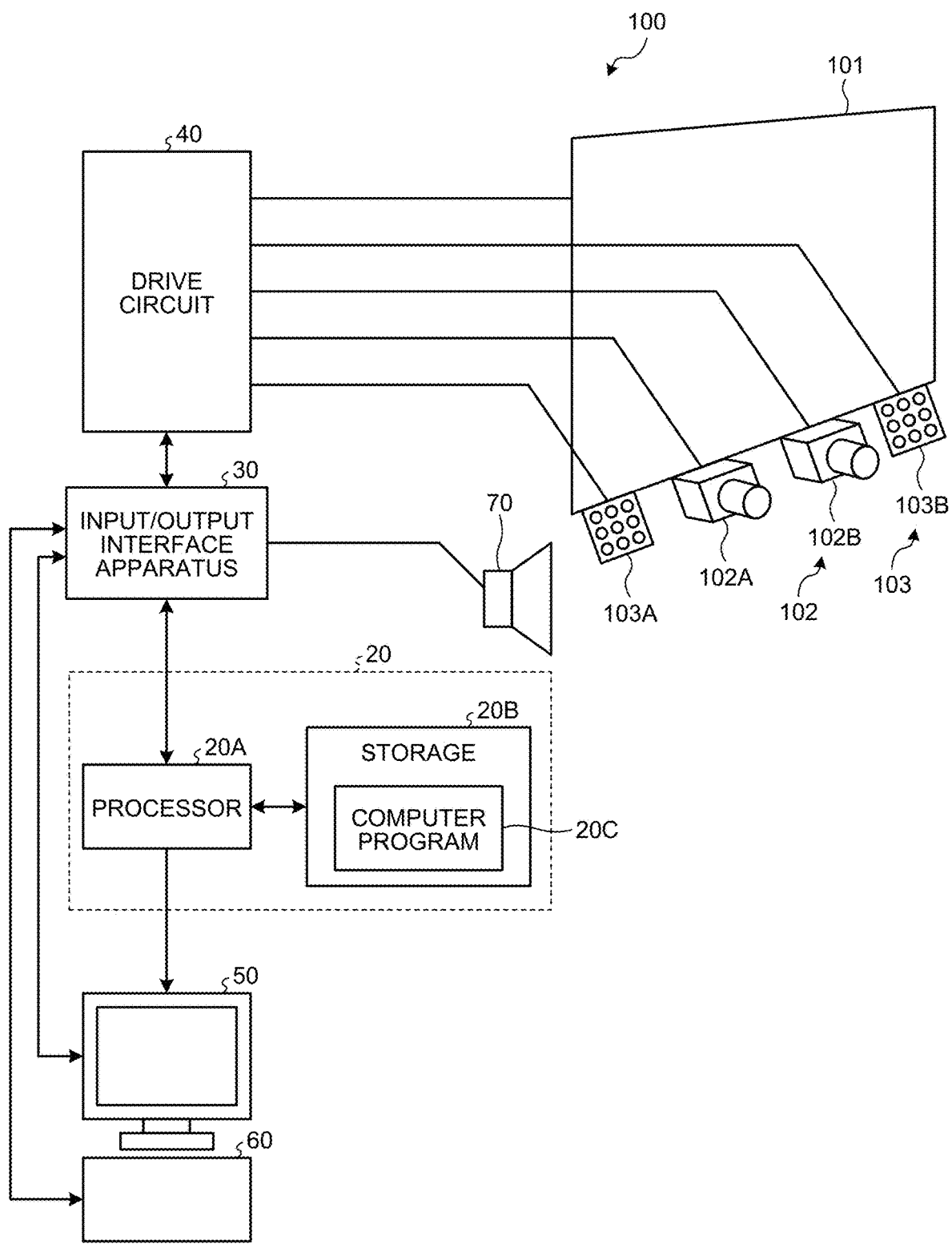
FIG. 2 is a diagram illustrating a hardware configuration example of the visual function detection apparatus according to the present embodiment.

FIG. 2 is a diagram illustrating a hardware configuration example of the visual function detection apparatus 100 according to the present embodiment. As illustrated in FIG. 2, the visual function detection apparatus 100 includes the display apparatus 101, the stereo camera apparatus 102, the illumination apparatus 103, a computer system 20, an input/output interface apparatus 30, a drive circuit 40, an output apparatus 50, and an input apparatus 60.

The computer system 20, the drive circuit 40, the output apparatus 50, and the input apparatus 60 perform data communication via the input/output interface apparatus 30. The computer system 20 includes a processor 20A and a storage 20B. The processor 20A includes a microprocessor such as a central processing unit (CPU). The storage 20B includes memories such as a read only memory (ROM) and random access memory (RAM) or a storage. The processor 20A performs processing in accordance with a computer program 20C stored in the storage 20B. The processor 20A executes the computer program 20C stored in the storage 20B to execute line-of-sight detection processing and thus can also serve as a line-of-sight detection apparatus according to the present embodiment.

The drive circuit 40 generates drive signals and outputs them to the display apparatus 101, the stereo camera apparatus 102, and the illumination apparatus 103. The drive circuit 40 supplies the image data of the eyeball 111 acquired by the stereo camera apparatus 102 to the computer system 20 via the input/output interface apparatus 30.

The output apparatus 50 includes a display apparatus such as a flat panel display. The output apparatus 50 may include a printing apparatus. The input apparatus 60 generates input data by being operated. The input apparatus 60 includes a keyboard or a mouse for a computer system. The input apparatus 60 may include a touch sensor provided on a display screen of the output apparatus 50 as the display apparatus.

In the present embodiment, the display apparatus 101 and the computer system 20 are separate apparatuses. The display apparatus 101 and the computer system 20 may be integral with each other. When the visual function detection apparatus 100 includes a tablet personal computer, for example, the tablet personal computer may come with the computer system 20, the input/output interface apparatus 30, the drive circuit 40, and the display apparatus 101.

Figure 3:
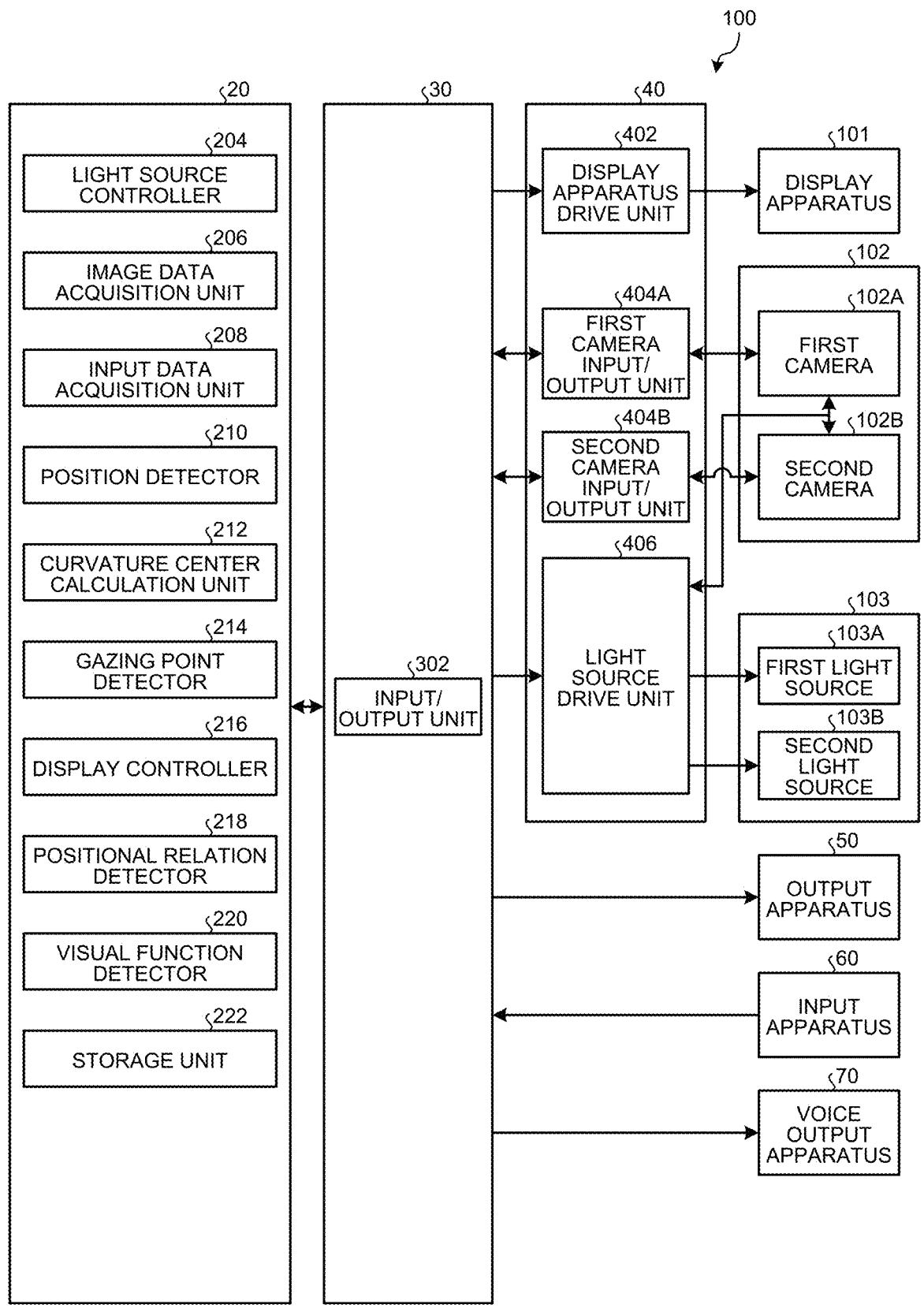
FIG. 3 is a functional block diagram illustrating an example of the visual function detection apparatus according to the present embodiment.

FIG. 3 is a functional block diagram illustrating an example of the visual function detection apparatus 100 according to the present embodiment. As illustrated in FIG. 3, the input/output interface apparatus 30 has an input/output unit 302. The drive circuit 40 includes: a display apparatus drive unit 402 that generates a drive signal to drive the display apparatus 101 to output the drive signal to the display apparatus 101; a first camera input/output unit 404A that generates a drive signal for driving the first camera 102A to output the drive signal to the first camera 102A; a second camera input/output unit 404B that generates a drive signal for driving the second camera 102B to output the drive signal to the second camera 102B; and a light source drive unit 406 that generates drive signals for driving the first light source 103A and the second light source 103B to output the drive signals to the first light source 103A and the second light source 103B. The first camera input/output unit 404A supplies the image data of the eyeball 111 acquired by the first camera 102A to the computer system 20 via the input/output unit 302. The second camera input/output unit 404B supplies the image data of the eyeball 111 acquired by the second camera 102B to the computer system 20 via the input/output unit 302.

The computer system 20 controls the visual function detection apparatus 100. The computer system 20 includes a light source controller 204, an image data acquisition unit 206, an input data acquisition unit 208, a position detector 210, a curvature center calculation unit 212, a gazing point detector 214, a display controller 216, a positional relation detector 218, a visual function detector 220, and a storage unit 222. The function of the computer system 20 is exhibited by the processor 20A and the storage 20B.

The light source controller 204 controls the light source drive unit 406 to control operating states of the first light source 103A and the second light source 103B. The light source controller 204 controls the first light source 103A and the second light source 103B such that the first light source 103A and the second light source 103B emit the detection light at different timings.

The image data acquisition unit 206 acquires the image data of the eyeball 111 of the test subject acquired by the stereo camera apparatus 102 including the first camera 102A and the second camera 102B from the stereo camera apparatus 102 via the input/output unit 302.

The input data acquisition unit 208 acquires the input data generated by the input apparatus 60 being operated from the input apparatus 60 via the input/output unit 302.

The position detector 210 detects position data of an iris center based on the image data of the eyeball 111 acquired by the image data acquisition unit 206. Further, the position detector 210 detects position data of a cornea reflection center based on the image data of the eyeball 111 acquired by the image data acquisition unit 206. The iris center is the center of the iris 112. The cornea reflection center is the center of the cornea reflection image 113. The position detector 210 detects the position data of the iris center and the position data of the cornea reflection center for each of right and left eyeballs 111 of the test subject.

The curvature center calculation unit 212 calculates position data of a cornea curvature center of the eyeball 111 based on the image data of the eyeball 111 acquired by the image data acquisition unit 206.

The gazing point detector 214 detects position data of a gazing point of the test subject based on the image data of the eyeball 111 acquired by the image data acquisition unit 206. In the present embodiment, the position data of the gazing point refers to position data of a point of intersection of a line-of-sight vector of the test subject and the display screen 101S of the display apparatus 101 defined in the three-dimensional global coordinate system. The gazing point detector 214 detects a line-of-sight vector of each of the right and left eyeballs 111 of the test subject based on the position data of the iris center and the position data of the cornea curvature center acquired from the image data of the eyeball 111. After the line-of-sight vector is detected, the gazing point detector 214 detects the position data of the gazing point indicating the point of intersection of the line-of-sight vector and the display screen 101S.

The display controller 216 outputs data to at least either the display apparatus 101 or the output apparatus 50. In the present embodiment, the display controller 216 outputs data for causing the display apparatus 101 to display the image 231 for determination to the display apparatus 101 to display the image 231 for determination on the display screen 101S of the display apparatus 101. The image 231 for determination displayed by the display controller 216 will be described below. The display controller 216 may cause the display screen 101S or the output apparatus 50 to display the position of the gazing point of each of the right and left eyeballs 111 of the test subject H.

The positional relation detector 218 detects a positional relation as information indicating a relation between a position of the image 231 for determination on the display screen 101S and the position of the gazing point detected by the gazing point detector 214. A method of detecting the positional relation will be described below.

The visual function detector 220 detects a visual function of the test subject H based on the positional relation detected by the positional relation detector 218. The visual function detector 220 detects the visual function by deriving information as a criterion for determining whether the image 231 for determination is seen by the test subject H based on the positional relation. That is, detecting the visual function here can be said to be deriving information as a criterion of determination whether the image 231 for determination can be visually recognized. The visual function detector 220 may derive information as a criterion for determining the eyesight of the test subject or derive information as a criterion for determining whether the test subject has cataract, for example, based on the determination whether the image 231 for determination is seen by the test subject H.

The storage unit 222 stores, for example, the position data of the gazing point detected by the gazing point detector 214, image data of the image (the image 231 for determination, for example) displayed on the display screen 101S, data on the positional relation detected by the positional relation detector 218, and data on a detection result of the visual function by the visual function detector 220.

The storage unit 222 stores a program causing a computer to execute processing to display an image on the display screen 101S, processing to detect the position of the gazing point of the test subject H observing the display screen 101S, processing to detect the positional relation between the position of the image 231 for determination and the position of the gazing point, and processing to detect the visual function based on the positional relation.

Figure 4:
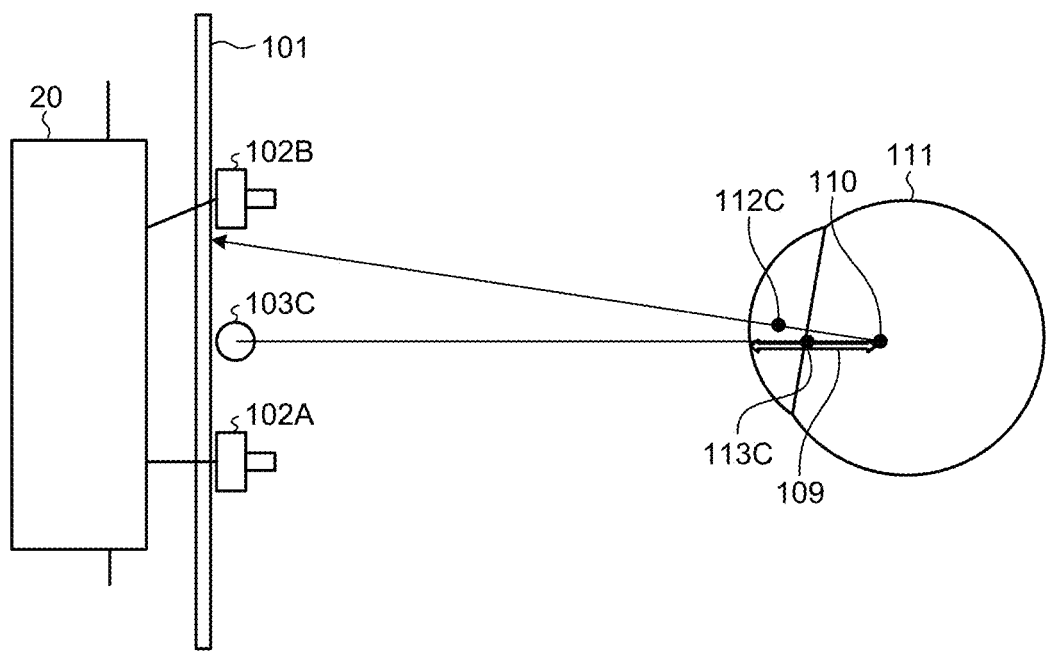
FIG. 4 is a schematic diagram for illustrating a method of calculating position data of a cornea curvature center according to the present embodiment.
Figure 5:
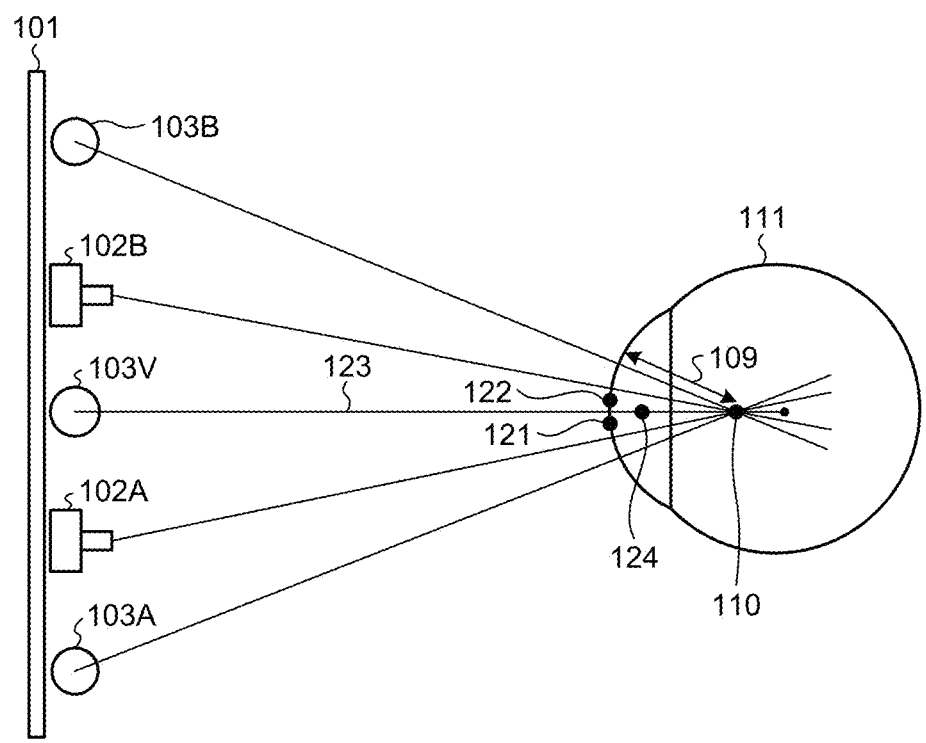
FIG. 5 is a schematic diagram for illustrating the method of calculating position data of a cornea curvature center according to the present embodiment.

The following describes an outline of processing by the curvature center calculation unit 212 according to the present embodiment. The curvature center calculation unit 212 calculates the position data of the cornea curvature center of the eyeball 111 based on the image data of the eyeball 111. FIG. 4 and FIG. 5 are schematic diagrams for illustrating a method of calculating position data of a cornea curvature center 110 according to the present embodiment. FIG. 4 illustrates an example in which the eyeball 111 is illuminated by one light source 103C. FIG. 5 illustrates an example in which the eyeball 111 is illuminated by the first light source 103A and the second light source 103B.

First, the following describes the example illustrated in FIG. 4. The light source 103C is placed between the first camera 102A and the second camera 102B. An iris center 112C is the center of the iris 112. A cornea reflection center 113C is the center of the cornea reflection image 113. In FIG. 4, the iris center 112C indicates an iris center when the eyeball 111 is illuminated by the one light source 103C. The cornea reflection center 113C indicates a cornea reflection center when the eyeball 111 is illuminated by the one light source 103C. The cornea reflection center 113C is present on a straight line connecting the light source 103C and the cornea curvature center 110. The cornea reflection center 113C is positioned at an intermediate point between a cornea surface and the cornea curvature center 110. A cornea curvature radius 109 is a distance between the cornea surface and the cornea curvature center 110. Position data of the cornea reflection center 113C is detected by the stereo camera apparatus 102. The cornea curvature center 110 is present on a straight line connecting the light source 103C and the cornea reflection center 113C. The curvature center calculation unit 212 calculates position data in which a distance from the cornea reflection center 113C on the straight line is a certain value as the position data of the cornea curvature center 110. The certain value is a value set in advance from a curvature radius value of a general cornea or the like and is stored in the storage unit 222.

The following describes the example illustrated in FIG. 5. In the present embodiment, the first camera 102A and the second light source 103B, and the second camera 102B and the first light source 103A are placed at positions laterally symmetric relative to a straight line passing through an intermediate position between the first camera 102A and the second camera 102B. It can be regarded that there is a virtual light source 103V at the intermediate position between the first camera 102A and the second camera 102B. A cornea reflection center 121 indicates a cornea reflection center in an image obtained by photographing the eyeball 111 with the second camera 102B. A cornea reflection center 122 indicates a cornea reflection center in an image obtained by photographing the eyeball 111 with the first camera 102A. A cornea reflection center 124 indicates a cornea reflection center corresponding to the virtual light source 103V. Position data of the cornea reflection center 124 is calculated based on position data of the cornea reflection center 121 and position data of the cornea reflection center 122 acquired by the stereo camera apparatus 102. The stereo camera apparatus 102 detects the position data of the cornea reflection center 121 and the position data of the cornea reflection center 122 in a three-dimensional local coordinate system defined in the stereo camera apparatus 102. Camera calibration by stereo calibration is performed on the stereo camera apparatus 102 in advance to calculate conversion parameters converting the three-dimensional local coordinate system of the stereo camera apparatus 102 into the three-dimensional global coordinate system. The conversion parameters are stored in the storage unit 222. The curvature center calculation unit 212 converts the position data of the cornea reflection center 121 and the position data of the cornea reflection center 122 acquired by the stereo camera apparatus 102 into position data in the three-dimensional global coordinate system using the conversion parameters. The curvature center calculation unit 212 calculates the position data of the cornea reflection center 124 in the three-dimensional global coordinate system based on the position data of the cornea reflection center 121 and the position data of the cornea reflection center 122 defined in the three-dimensional global coordinate system. The cornea curvature center 110 is present on a straight line 123 connecting the virtual light source 103V and the cornea reflection center 124. The curvature center calculation unit 212 calculates position data in which a distance from the cornea reflection center 124 on the straight line 123 is a certain value as the position data of the cornea curvature center 110. The certain value is a value set in advance from a curvature radius value of a general cornea or the like and is stored in the storage unit 222.

Thus, even when there are two light sources, the cornea curvature center 110 can be calculated by a method similar to the method when there is one light source.

The cornea curvature radius 109 is a distance between the cornea surface and the cornea curvature center 110. Consequently, position data of the cornea surface and the position data of the cornea curvature center 110 are calculated, whereby the cornea curvature radius 109 is calculated.

Figure 6:
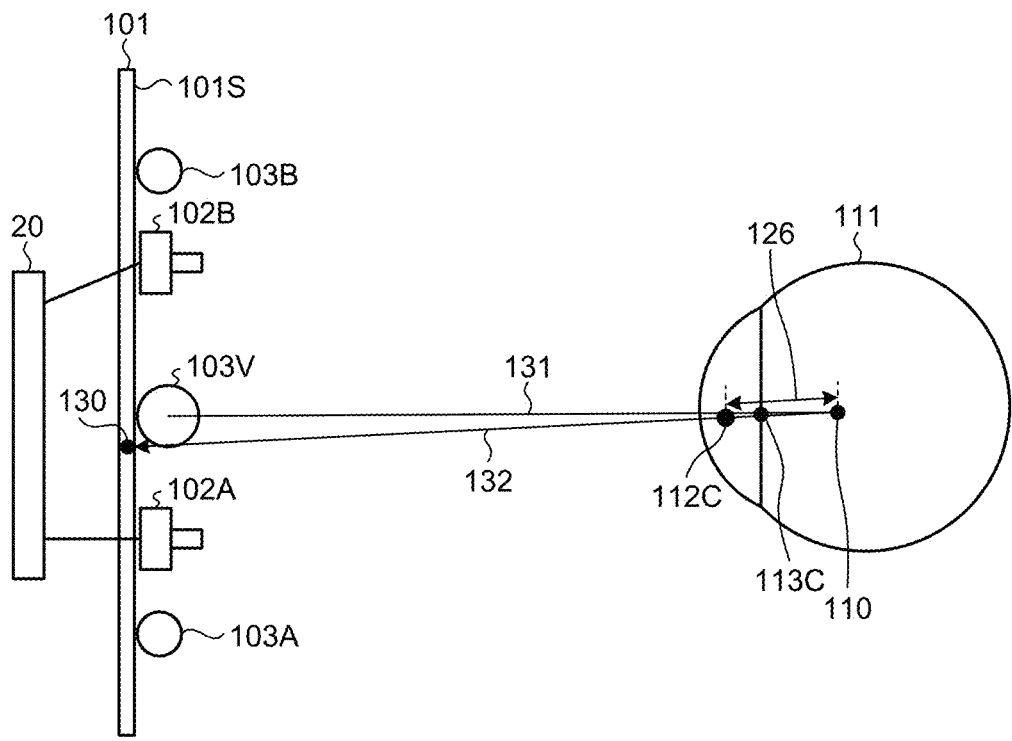
FIG. 6 is a schematic diagram for illustrating an example of calibration processing according to the present embodiment.

The following describes an exemplary method of detecting a line of sight according to the present embodiment. FIG. 6 is a schematic diagram for illustrating an example of calibration processing according to the present embodiment. In the calibration processing, a target position 130 is set in order to cause the test subject to gaze it. The target position 130 is defined in the three-dimensional global coordinate system. In the present embodiment, the target position 130 is set at a central position of the display screen 101S of the display apparatus 101, for example. The target position 130 may be set at an end position of the display screen 101S. An output controller 226 displays a target image at the set target position 130. A straight line 131 is a straight line connecting the virtual light source 103V and the cornea reflection center 113C. A straight line 132 is a straight line connecting the target position 130 and the iris center 112C. The cornea curvature center 110 is a point of intersection of the straight line 131 and the straight line 132. The curvature center calculation unit 212 can calculate the position data of the cornea curvature center 110 based on position data of the virtual light source 103V, position data of the target position 130, position data of the iris center 112C, and position data of the cornea reflection center 113C.

Figure 7:
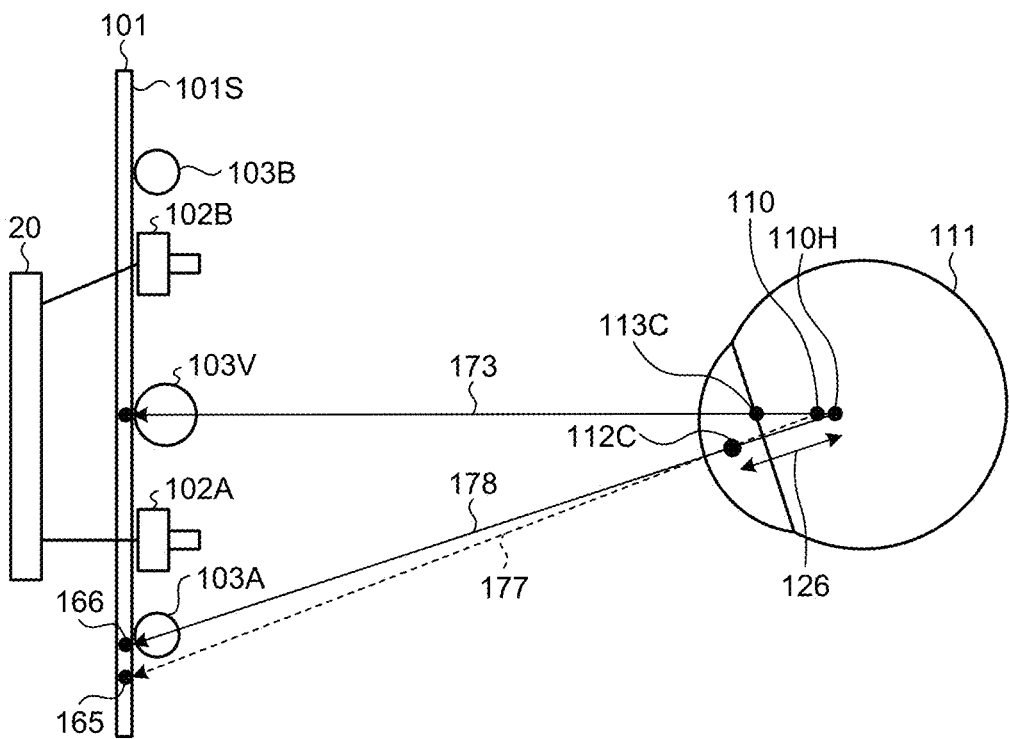
FIG. 7 is a schematic diagram for illustrating an example of gazing point detection processing according to the present embodiment.

The following describes gazing point detection processing. The gazing point detection processing is performed after the calibration processing. The gazing point detector 214 calculates the line-of-sight vector of the test subject and the position data of the gazing point based on the image data of the eyeball 111. FIG. 7 is a schematic diagram for illustrating an example of gazing point detection processing according to the present embodiment. In FIG. 7, a gazing point 165 indicates a gazing point determined from a cornea curvature center calculated using a general curvature radius value. A gazing point 166 indicates a gazing point determined from a cornea curvature center calculated using a distance 126 determined by the calibration processing. The iris center 112C indicates an iris center calculated in the calibration processing, whereas the cornea reflection center 113C indicates a cornea reflection center calculated in the calibration processing. A straight line 173 is a straight line connecting the virtual light source 103V and the cornea reflection center 113C. The cornea curvature center 110 is in a position of a cornea curvature center calculated from the general curvature radius value. The distance 126 is a distance between the iris center 112C calculated by the calibration processing and the cornea curvature center 110. A cornea curvature center 110H indicates a position of a corrected cornea curvature center obtained by correcting the cornea curvature center 110 using the distance 126. The cornea curvature center 110H is determined by the presence of the cornea curvature center 110 on the straight line 173 and the distance between the iris center 112C and the cornea curvature center 110 being the distance 126. Thus, a line of sight 177 calculated when the general curvature radius value is used is corrected to a line of sight 178. The gazing point on the display screen 101S of the display apparatus 101 is corrected from the gazing point 165 to the gazing point 166.

(Method of Detecting Visual Function)

Figure 8:
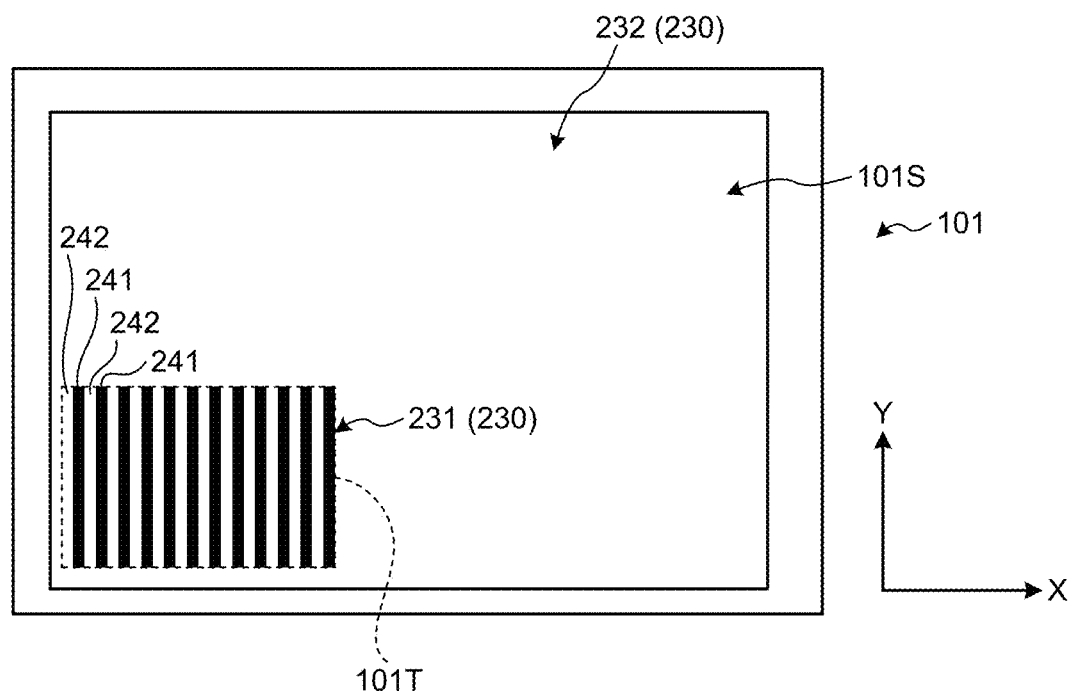
FIG. 8 is a diagram illustrating an image for determination according to the present embodiment.
Figure 9:
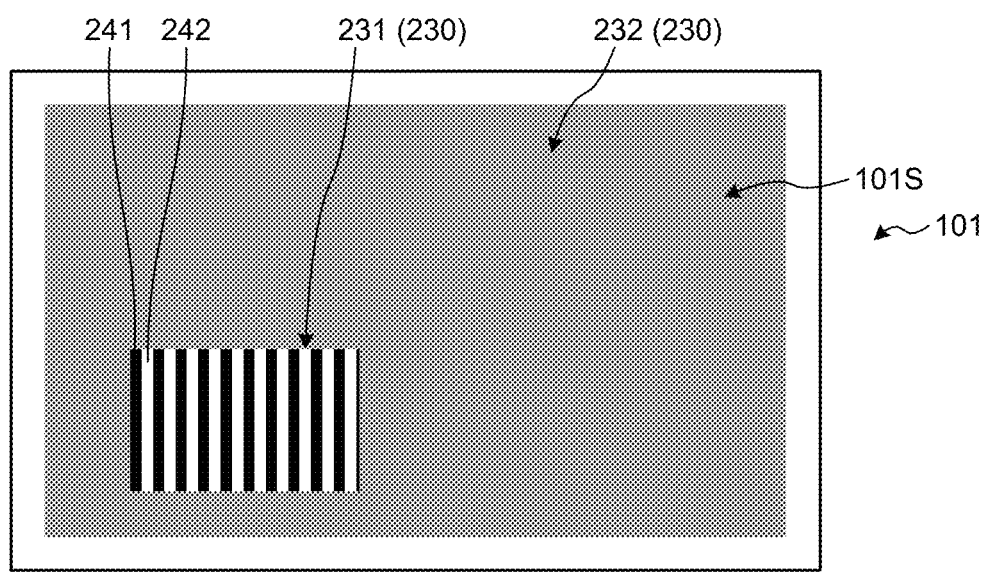
FIG. 9 is a diagram illustrating the image for determination according to the present embodiment.

The following describes a method of detecting a visual function according to the present embodiment. FIG. 8 and FIG. 9 are diagrams each illustrating an image for determination according to the present embodiment. When the visual function detection is performed, the display controller 216 outputs data for causing the display apparatus 101 to display an image 230 to the display apparatus 101 to display the image 230 on the display screen 101S of the display apparatus 101. As illustrated in FIG. 8, the image 230 includes the image 231 for determination and an image 232 for background. That is, it can be said that the display controller 216 outputs data for causing the display apparatus 101 to display the image 231 for determination and data for causing the display apparatus 101 to display the image 232 for background, thereby causing the image 231 for determination and the image 232 for background to be displayed on the display screen 101S of the display apparatus 101. While the image 230 is an image occupying the entire region of the display screen 101S, it may be an image occupying part of the display screen 101S.

As illustrated in FIG. 8, the image 231 for determination is displayed within a display region 101T as a partial region within a region in which the image 230 is displayed (the display screen 101S in this example). That is, the image 231 for determination is displayed so as to occupy the entire region of the display region 101T as the partial region of the display screen 101S. The display controller 216 changes a display position of the image 231 for determination, i.e., a position of the display region 101T within the display screen 101S. The image 231 for determination is preferably 0.5 times or less as large as the display screen 101S. Thus, when the position of the display region 101T is switched, display regions 101T can be prevented from overlapping with each other. The image 231 for determination is more preferably 0.25 times or less as large as the display screen 101S. Thus, flexibility in positional change in both the X-axial direction and the Y-axial direction can be increased. However, the size of the display region 101T can be set to any size.

The image 231 for determination is an image displaying a pattern. Specifically, the image 231 for determination includes first images 241 and second images 242. In other words, the display region 101T is sectioned into a first region, in which the first images 241 are displayed, and a second region, in which the second images 242 are displayed. Consequently, the first images 241 can also be referred to as the first region, in which the first images 241 are displayed, whereas the second images 242 can also be referred to as the second region, in which the second images 242 are displayed. The first images 241 and the second images 242 are images different from each other in luminance. In the present embodiment, the first images 241 are images lower in luminance than the second images 242. In the example of the present embodiment, the first images 241 and the second images 242 are gray images. Consequently, the first images 241 have more black components than the second images 242, whereas the second images 242 have more white components than the first images 241. However, the first images 241 and the second images 242 may be colored images so long as they are images different from each other in luminance.

As illustrated in FIG. 8, in the present embodiment, the image 231 for determination includes a plurality of first images 241 and second images 242, in which the first images 241 and the second images 242 are arranged alternately in stripes. That is, the first images 241 and the second images 242 have a length along the Y-axial direction the same as a length of the display region 101T along the Y-axial direction and extend from an upper end to a lower end of the display region 101T along the Y-axial direction. The first images 241 and the second images 242 have a length (width) along the X-axial direction shorter than a length of the display region 101T along the X-axial direction. The first images 241 and the second images 242 are alternately arranged along the X-axial direction within the display region 101T. In the present embodiment, the first images 241 are equal to each other in area, and the second images 242 are also equal to each other in area. Each of the first images 241 and each of the second images 242 are also equal to each other in area. The number of the first images 241 and the number of the second images 242 are also the same with each other. However, the first images 241 may be different from each other in area and shape, and the second images 242 may also be different from each other in area and shape. The number of the first images 241 and the number of the second images 242 may also be different from each other.

As illustrated in FIG. 8, the image 232 for background is an image displayed in a region other than the display region 101T in which the image 231 for determination is displayed within the region in which the image 230 is displayed (the display screen 101S in this example). That is, the image 232 for background is an image displayed so as to surround the display region 101T (the image 231 for determination). The image 232 for background is displayed so as to occupy the entire region other than the display region 101T in the region in which the image 230 is displayed. However, the image 232 for background only needs to surround the display region 101T, and may occupy part of the region other than the display region 101T.

In the example illustrated in FIG. 8, the image 232 for background is white for the convenience of description. However, the image 232 for background actually has a color illustrated in FIG. 9 for the reason of a relation with the image 231 for determination in luminance. That is, as illustrated in FIG. 9, the image 232 for background has average luminance matching average luminance of the image 231 for determination. The average luminance of the image 231 for determination is an average of luminance of each position (luminance of each pixel) of the image 231 for determination. The average luminance of the image 231 for determination is a value obtained by totaling the luminance of each position (luminance of each pixel) of the image 231 for determination and dividing the total by the total number of the pixels of the image 231 for determination, for example. Similarly, the average luminance of the image 232 for background is also an average of luminance of each position (luminance of each pixel) of the image 232 for background and is a value obtained by totaling the luminance of each position (luminance of each pixel) of the image 232 for background and dividing the total by the total number of the pixels of the image 232 for background, for example. Although the average luminance of the image 232 for background and the average luminance of the image 231 for determination do not necessarily match each other, the difference between the average luminance of the image 232 for background and the average luminance of the image 231 for determination is preferably 20% or less relative to either the average luminance of the image 232 for background or the image 231 for determination.

The image 232 for background is a uniform image with no pattern. In the present embodiment, the image 232 for background is an image with constant luminance across the entire region and is further an image having the same color as that of the image 231 for determination, i.e., a gray image. Consequently, the image 232 for background is higher in luminance and has more white components than the first images 241. The image 232 for background is lower in luminance and has more black components than the second images 242. In the following, for the convenience of description, some drawings are different in the relation between the image 232 for background and the first images 241 and the second images 242 in luminance from FIG. 9. However, it is preferable that the relation actually be the relation illustrated in FIG. 9.

Figure 10:
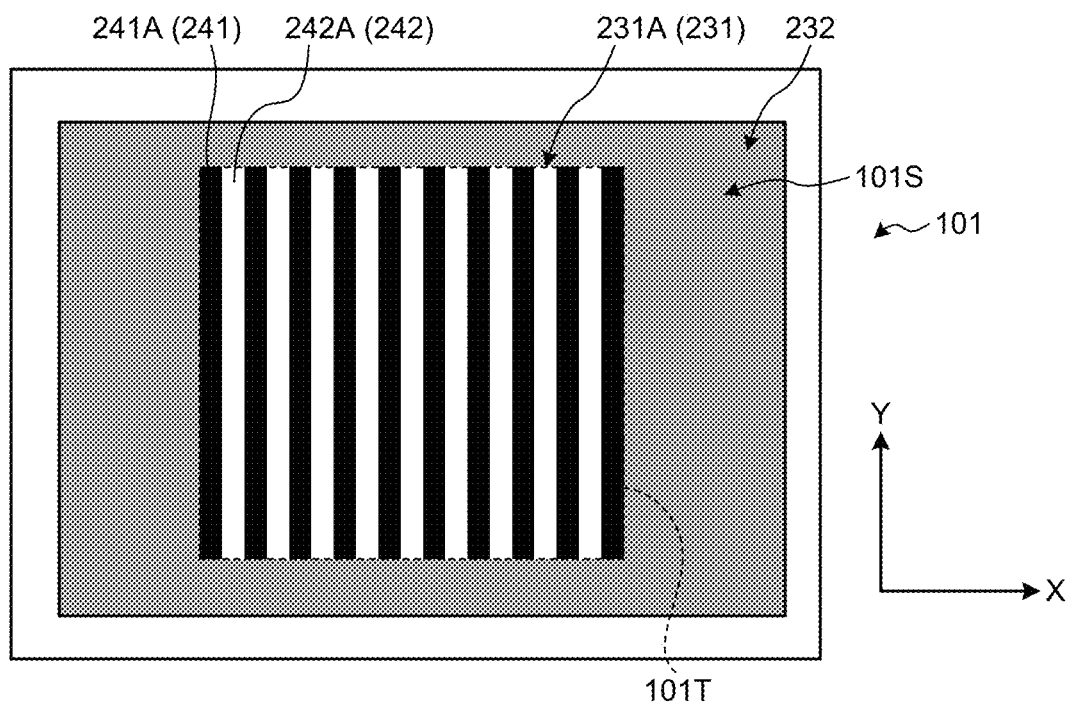
FIG. 10 is a diagram illustrating a case in which display of the image for determination is changed.
Figure 11:
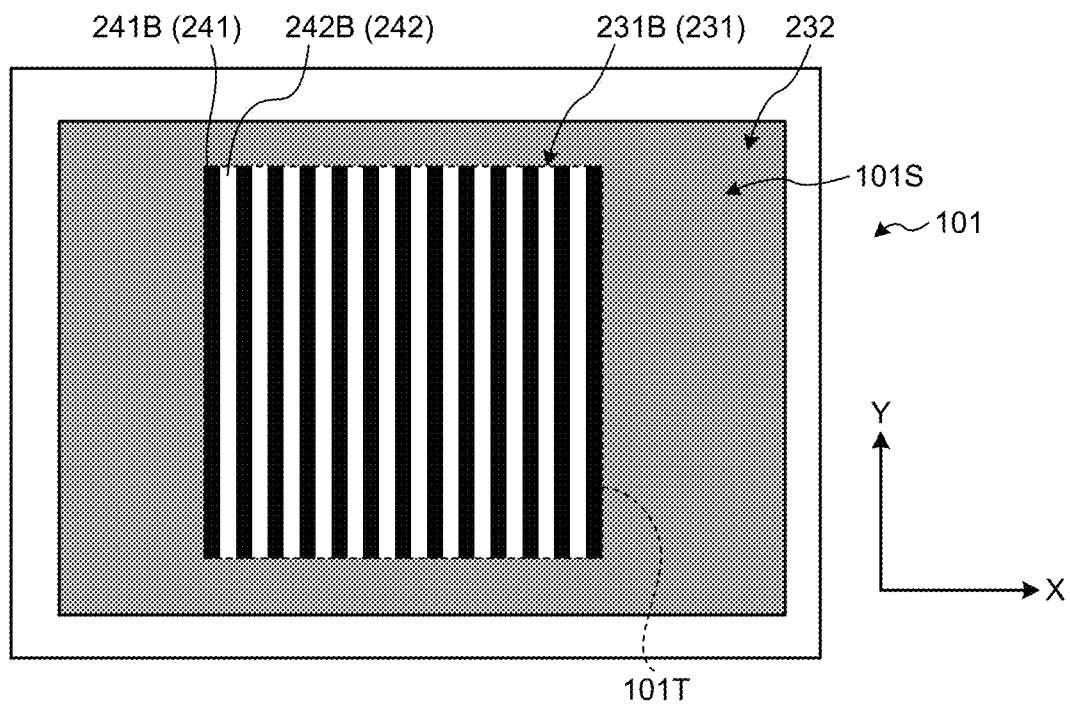
FIG. 11 is a diagram illustrating a case in which display of the image for determination is changed.
Figure 12:
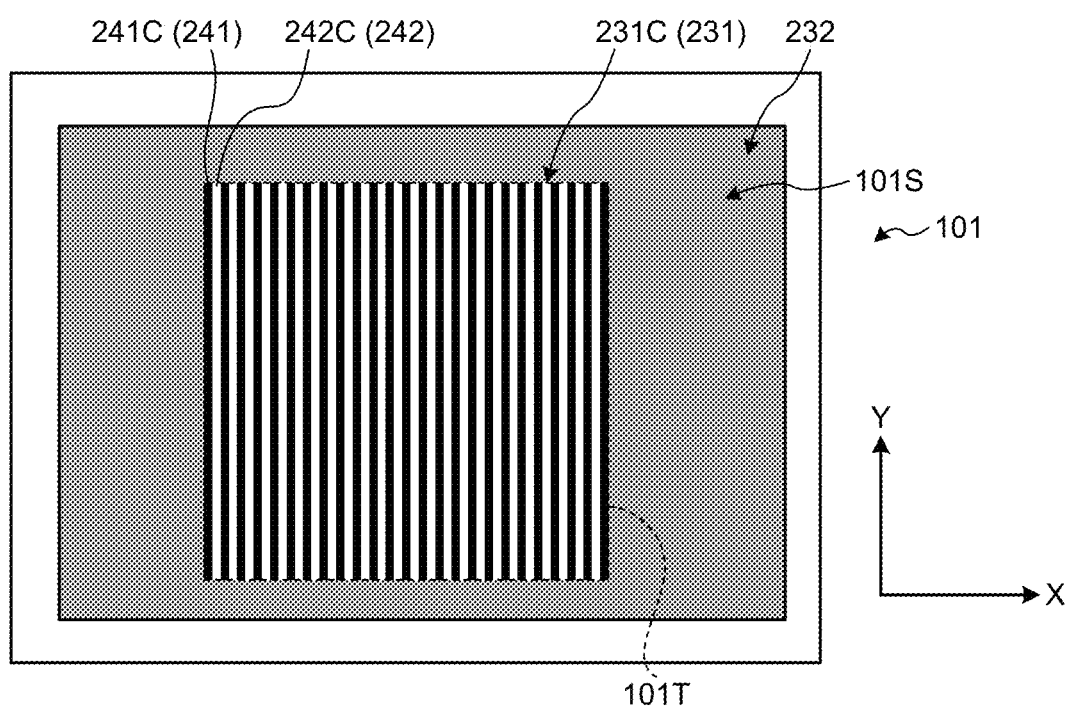
FIG. 12 is a diagram illustrating a case in which display of the image for determination is changed.

FIG. 10 to FIG. 12 are diagrams each illustrating cases in which display of the image for determination is changed. The display controller 216 may display the image 231 for determination with different patterns as illustrated in FIG. 10 to FIG. 12, for example, for a visual function detection examination. While in FIG. 10 to FIG. 12, the size of the display region 101T, i.e., the image 231 for determination is larger than that in FIG. 8 for the convenience of description, the display region 101T is actually as large as described with reference to FIG. 8. An image 231A for determination illustrated in FIG. 10, an image 231B for determination illustrated in FIG. 11, and an image 231C for determination illustrated in FIG. 12 are different from each other in the size (area) of the first images 241 and the second images 242 and are also different from each other in the number of the first images 241 and the second images 242. That is, the images 231A, 231B, and 231C for determination are different from each other in the density distribution of the first images 241 and the second images 242. While the image 231A for determination, the image 231B for determination, and the image 231C for determination are equal to each other in the entire size, i.e., the size of the display region 101T, they may be different from each other in size.

In the examples in FIG. 10 to FIG. 12, first images 241B and second images 242B of the image 231B for determination are smaller in area than first images 241A and second images 242A of the image 231A for determination. Further, a length of the first images 241B and the second images 242B along the X-axial direction is shorter than a length of the first images 241A and the second images 242A along the X-axial direction. In the image 231B for determination, the number of the first images 241B and the second images 242B is larger than that of the first images 241A and the second images 242A of the image 231A for determination. First images 241C and second images 242C of the image 231C for determination are smaller in area than the first images 241B and the second images 242B of the image 231B for determination. Further, a length of the first images 241C and the second images 242C along the X-axial direction is shorter than a length of the first images 241B and the second images 242B along the X-axial direction. In the image 231C for determination, the number of the first images 241C and the second images 242C is larger than that of the first images 241B and the second images 242B of the image 231B for determination.

The image 231B for determination illustrated in FIG. 11, in which the first images 241 and the second images 242 are smaller than those of the image 231A for determination illustrated in FIG. 10, is more difficult for the test subject to visually recognize than the image 231A for determination. Similarly, the image 231C for determination illustrated in FIG. 12 is more difficult for the test subject to visually recognize than the image 231B for determination. Consequently, the display controller 216 thus displays the image 231 for determination with different patterns and can thereby detect the degree of the visual function (eyesight, for example) of the test subject H step by step.

When the visual function detection is performed, the display controller 216 thus causes the image 231 for determination and the image 232 for background to be displayed on the display screen 101S of the display apparatus 101. During the visual function detection, the test subject H observes the display screen 101S, and the gazing point detector 214 detects the gazing point 166 of the test subject H at that time. The positional relation detector 218 detects a positional relation indicating a relation between the position of the image 231 for determination on the display screen 101S and the position of the gazing point detected by the gazing point detector 214, and the visual function detector 220 detects the visual function of the test subject H based on a detection result of the positional relation. The following describes the flow detecting the visual function.

Figure 13:
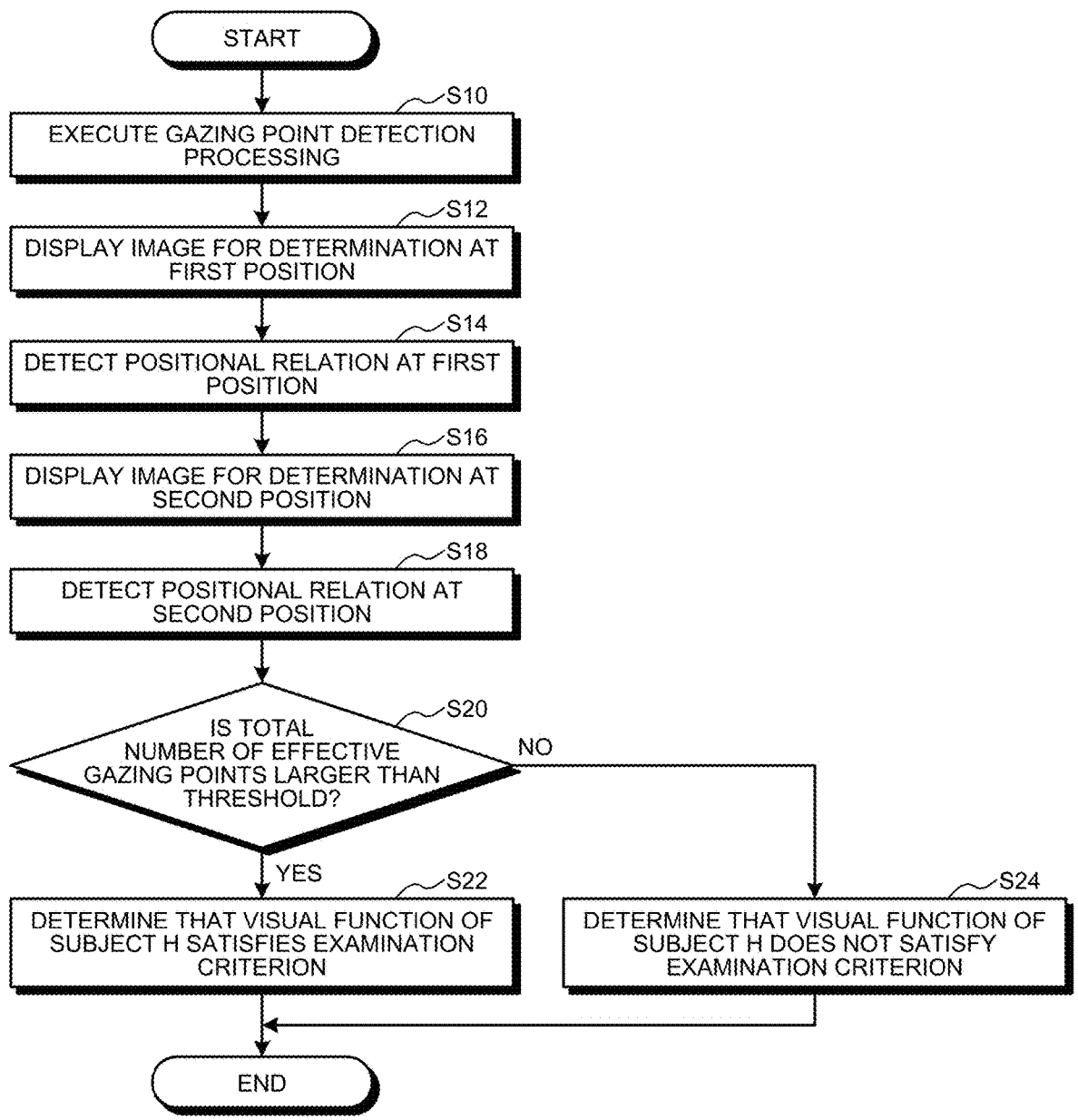
FIG. 13 is a flowchart illustrating the flow of detecting a visual function.

FIG. 13 is a flowchart illustrating the flow of detecting the visual function. FIG. 14 is a diagram for illustrating a display position of the image for determination. As illustrated in FIG. 13, when the visual function detection is performed, the gazing point detector 214 executes the gazing point detection processing described above (Step S10) to detect a position of the gazing point 166 of the test subject H positioned in front of the display screen 101S. The image data of the eyeball 111 of the test subject is acquired every certain time by photographing by the image data acquisition unit 206. Consequently, the gazing point detector 214 detects the position of the gazing point 166 every certain time. This certain time is about ⅟60 second, for example, and thus the gazing point 166 is detected about 60 times per second. However, this certain time has any duration. The gazing point detector 214 continues position detection of the gazing point 166 over a period during which the image 231 for determination is displayed, which will be described below.

The display controller 216 displays the image 231 for determination at a first position P1 (Step S12). The gazing point detector 214 performs position detection of the gazing point 166 while the image 231 for determination is displayed at the first position P1. In the example in FIG. 14, the first position P1 is at the lower left side, which is a mere example. That is, the first position P1 is any position on the display screen 101S. The display controller 216 randomly selects the first position P1 from the display screen 101S and displays the image 230 such that the display region 101T is positioned at the first position P1. Thus, the image 231 for determination out of the image 230 is displayed within the display region 101T positioned at the first position P1, whereas the image 232 for background out of the image 230 is displayed outside the display region 101T.

The display controller 216 continues to display the image 231 for determination at the first position P1 for a certain period. That is, in the present embodiment, the image 231 for determination is a still image. This certain period is any duration set in advance, which is about 1 second or more and 3 seconds or less, for example. However, the period during which the image 231 for determination is continued to be displayed at the first position P1 and a frame rate for the gazing point 166 detection are set such that the gazing point 166 can be detected a plurality of times while the image 231 for determination is displayed at the first position P1. That is, the gazing point 166 is detected a plurality of times in the period during which the image 231 for determination is displayed at the first position P1. In the following, the period during which the image 231 for determination is displayed at the first position P1 will be defined as a first period.

Upon the end of display of the image 231 for determination at the first position P1, the positional relation detector 218 detects the positional relation at the first position P1 (Step S14). The positional relation detector 218 calculates the positional relation based on the position data of the gazing point 166 detected by the gazing point detector 214 and the position data of the display region 101T of the image 231 for determination displayed by the display controller 216. Specifically, the positional relation detector 218 detects whether the gazing point 166 detected within the first period is present within the display region 101T of the image 231 for determination at the first position P1 and detects the gazing point 166 present within the display region 101T as an effective gazing point. The positional relation detector 218 similarly detects whether all gazing points 166 detected in the first period are present within the display region 101T to detect effective gazing points from all the gazing points 166 within the first period. The positional relation detector 218 sets the number of the effective gazing points in the first period as the positional relation at the first position P1. In other words, the positional relation detector 218 detects the number of gazing points present within the display region 101T of the image 231 for determination at the first position P1 among the gazing points 166 detected in the first period and sets the number as the positional relation at the first position P1.

Upon the end of detection of the positional relation at the first position P1, the display controller 216 displays the image 231 for determination at a second position P2 (Step S16). The gazing point detector 214 performs position detection of the gazing point 166 while the image 231 for determination is displayed at the second position P2. While in the example in FIG. 14, the second position P2 is at the upper right side, the second position P2 is any position so long as being on the display screen 101S different from the first position P1. That is, the display controller 216 randomly selects the second position P2 from the display screen 101S so as to be a position different from the first position P1 and displays the image 230 such that the display region 101T is positioned at the second position P2. Thus, the image 231 for determination out of the image 230 is displayed within the display region 101T positioned at the second position P2, whereas the image 232 for background out of the image 230 is displayed outside the display region 101T. Thus, the image 231 for determination displayed at the second position P2 and the image 231 for determination displayed at the first position P1 are different in position to be displayed. The display controller 216 may display the image 231 for determination at the second position P2 after display of the image 231 for determination at the first position P1 or may display the image 231 for determination before or during detection of the positional relation at the first position P1, for example.

The display controller 216 continues to display the image 231 for determination at the second position P2 for the same time as the first period (the display time at the first position P1). Consequently, the gazing point 166 is detected a plurality of times in a period during which the image 231 for determination is displayed at the second position P2. A display period of the image 231 for determination at the second position P2 may be different from the first period. In the following, the display period of the image 231 for determination at the second position P2 will be referred to as a second period.

In the present embodiment, upon the end of the first period, the display controller 216 switches display from the image 231 for determination at the first position P1 to the image 231 for determination at the second position P2. That is, upon the end of the first period, the display controller 216 ends display of the image 231 for determination at the first position P1 and then displays the image 231 for determination at the second position P2. Consequently, at the timing when the image 231 for determination is displayed at second position P2, the image 231 for determination at the first position P1 is not displayed. Thus, the display controller 216 causes the first period and the second period not to overlap with each other but may cause them to slightly overlap with each other.

The display region 101T of the image 231 for determination at the second position P2 and the display region 101T of the image 231 for determination at the first position P1 are preferably not displayed at positions overlapping with each other. However, the display region 101T of the image 231 for determination at the second position P2 and the display region 101T of the image 231 for determination at the first position P1 may be set such that partial regions overlap with each other.

The image 231 for determination at the second position P2 is preferably the same image as the image 231 for determination at the first position P1. That is, the image 231 for determination at the second position P2 has the same size and number of the first images 241 and the second images 242 as the size and number of the first images 241 and the second images 242 of the image 231 for determination at the first position P1. When the image 231 for determination at the first position P1 is the image 231A for determination illustrated in FIG. 10, for example, the image 231 for determination at the second position P2 is also the image 231A for determination. The display region 101T of the image 231 for determination at the second position P2 and the display region 101T of the image 231 for determination at the first position P1 are also preferably equal to each other. However, the image 231 for determination at the second position P2 and the image 231 for determination at the first position P1 may be different from each other in the size of the display region 101T.

The first position P1 and the second position P2 may be information indicating coordinates on the display screen 101S or information indicating any one of a plurality of regions as a result of dividing the display screen 101S, for example.

Upon the end of display of the image 231 for determination at the second position P2, the positional relation detector 218 detects the positional relation at the second position P2 (Step S18). The positional relation detector 218 calculates the positional relation based on the position data of the gazing point 166 detected by the gazing point detector 214 and the position data of the display region 101T of the image 231 for determination displayed by the display controller 216. Specifically, the positional relation detector 218 detects whether the gazing point 166 detected within the second period is present within the display region 101T of the image 231 for determination at the second position P2 and defines the gazing point 166 present within the display region 101T as the effective gazing point. The positional relation detector 218 similarly detects whether all gazing points 166 detected within the second period are present within the display region 101T to detect effective gazing points from all the gazing points 166 in the second period. The positional relation detector 218 defines the number of the effective gazing points in the second period as the positional relation at the second position P2. In other words, the positional relation detector 218 detects the number of gazing points present within the display region 101T of the image 231 for determination at the second position P2 among the gazing points 166 detected in the second period and defines the number as the positional relation at the second position P2.

Thus, in the present embodiment, upon the end of the display of the image 231 for determination at the first position P1, the positional relation at the first position P1 is detected before display of the image 231 for determination at the second position P2. However, the positional relation detector 218 may collectively detect the positional relations at the first position P1 and the second position P2, after display of the image 231 for determination at the first position P1 and display of the image 231 for determination at the second position P2 end.

Upon the end of detection of the positional relation at the second position P2 at Step S18, the visual function detector 220 performs determination of the visual function of the test subject H based on the positional relation. Specifically, the visual function detector 220 determines whether the total number of the effective gazing points at the first position P1 and the effective gazing points at the second position P2 is larger than a threshold set in advance (Step S20). If the total number is larger than the threshold (Yes at Step S20), the visual function detector 220 determines that the visual function of the test subject H satisfies an examination criterion (Step S22). On the other hand, if the total number is not larger than the threshold (No at Step S20), i.e., the threshold or less, the visual function detector 220 determines that the visual function of the test subject H does not satisfy the examination criterion (Step S24). With Step S22 or S24, the processing ends. When the threshold is 90, the number of the effective gazing points at the first position P1 is 50, and the number of the effective gazing points at the second position P2 is 60, for example, the total number is 110, which is greater than the threshold. In this case, the visual function of the test subject H is determined to satisfy the examination criterion. The visual function detector 220 derives this determination result about whether the visual function of the test subject H satisfies the examination criterion as information as a criterion for detecting the visual function and stores the information in the storage unit 222, for example.

While in the present embodiment, examinations are performed at two positions, or the first position P1 and the second position P2, the number of positions at which examinations are performed is not limited to two. The number of positions at which examinations are performed, i.e., the number of positions at which the image 231 for determination is displayed may be one, for example. The number of positions at which the image 231 for determination is displayed may be three or more. That is, the second position P2 as a position different from the first position P1 includes a plurality of positions. The image 231 for determination may be displayed at the positions at the same timing. The positional relation detector 218 also calculates the number of the effective gazing points at the third and subsequent positions, and the visual function detector 220 performs determination with the number of the effective gazing points also added to the total number described above.

Figure 15:
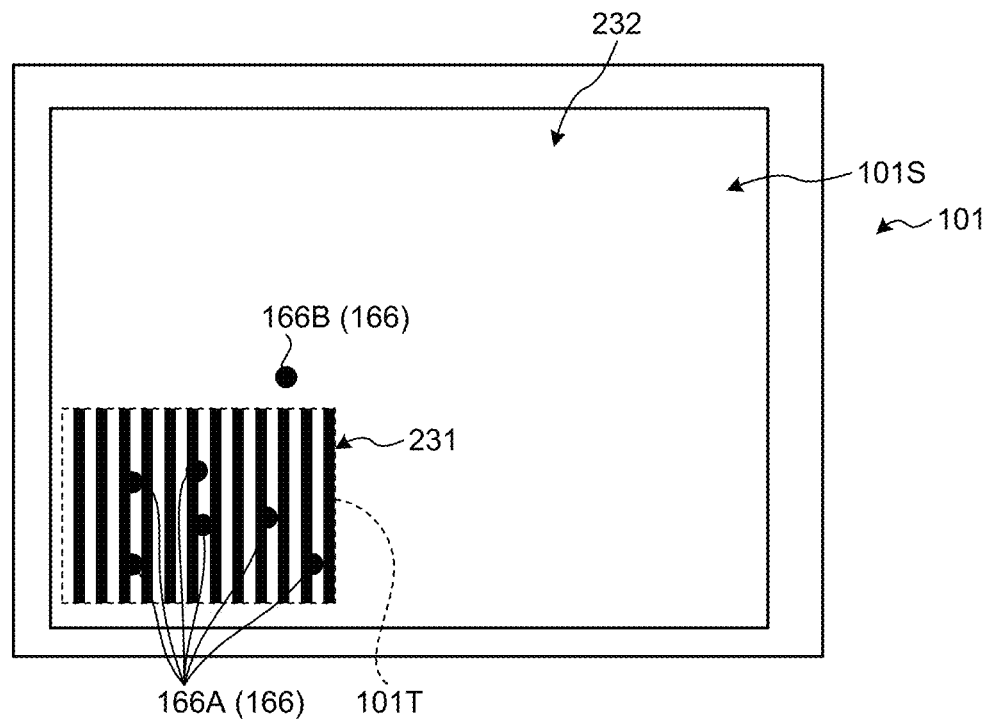
FIG. 15 is a diagram illustrating a positional relation between gazing points and the image for determination.
Figure 16:
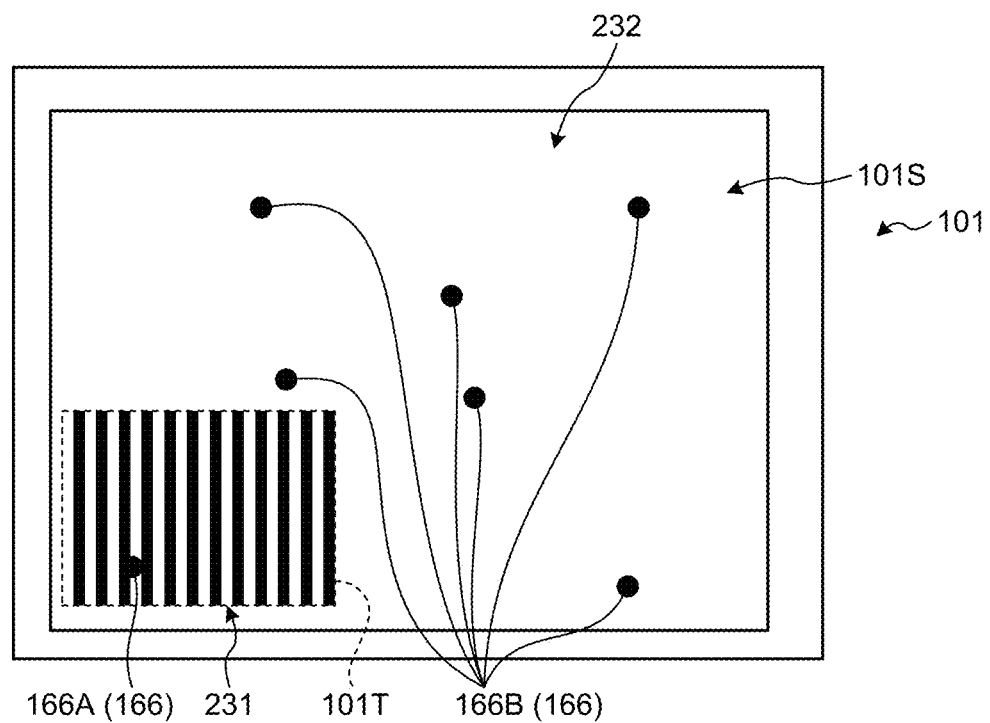
FIG. 16 is a diagram illustrating the positional relation between the gazing points and the image for determination.

FIG. 15 and FIG. 16 are diagrams each illustrating the positional relation between the gazing points and the image for determination. The image 231 for determination displayed on the display screen 101S is an image attracting the attention of the test subject H. Consequently, when the test subject H can visually recognize the image 231 for determination, the test subject H directs the line of sight to the image 231 for determination. On the other hand, when the test subject H cannot visually recognize the image 231 for determination, the test subject H does not direct the line of sight to the image 231 for determination, and the line of sight may vary. In the present embodiment, whether the test subject H can visually recognize the image 231 for determination is determined based on the positional relation between the position of the gazing point of the test subject H and the image 231 for determination, whereby the visual function of the test subject H is detected.

Gazing points 166A in FIG. 15 are the gazing points 166 positioned within the display region 101T of the image 231 for determination, whereas a gazing point 166B is the gazing point 166 positioned outside the display region 101T of the image 231 for determination. In the example in FIG. 15, the number of the gazing points 166A is larger, and the line of sight is concentrated on the vicinity of the display region 101T, and thus the visual function detector 220 determines that the test subject H can visually recognize the image 231 for determination and determines that the visual function of the test subject H satisfies the examination criterion. On the other hand, in the example in FIG. 16, the number of the gazing point 166A is smaller, whereas the number of gazing points 166B is larger, and thus the visual function detector 220 determines that the test subject H cannot visually recognize the image 231 for determination and determines that the visual function of the test subject H does not satisfy the examination criterion.

Even when the test subject H cannot visually recognize the image 231 for determination, the test subject H may gaze at a point in a concentrated manner, and there is a possibility that the gazing point is accidentally concentrated on the image 231 for determination. Given this situation, the visual function detection apparatus 100 according to the present embodiment displays the image 231 for determination at the first position P1 and the second position P2 at separate timings, and detects the gazing point 166 at the respective timings. The visual function detection apparatus 100 thus changes the position of the image 231 for determination to reduce contingency in which the gazing point is concentrated on the image 231 for determination even though the test subject H cannot visually recognize the image 231 for determination, thereby improving visual function detection accuracy.

Figure 17:
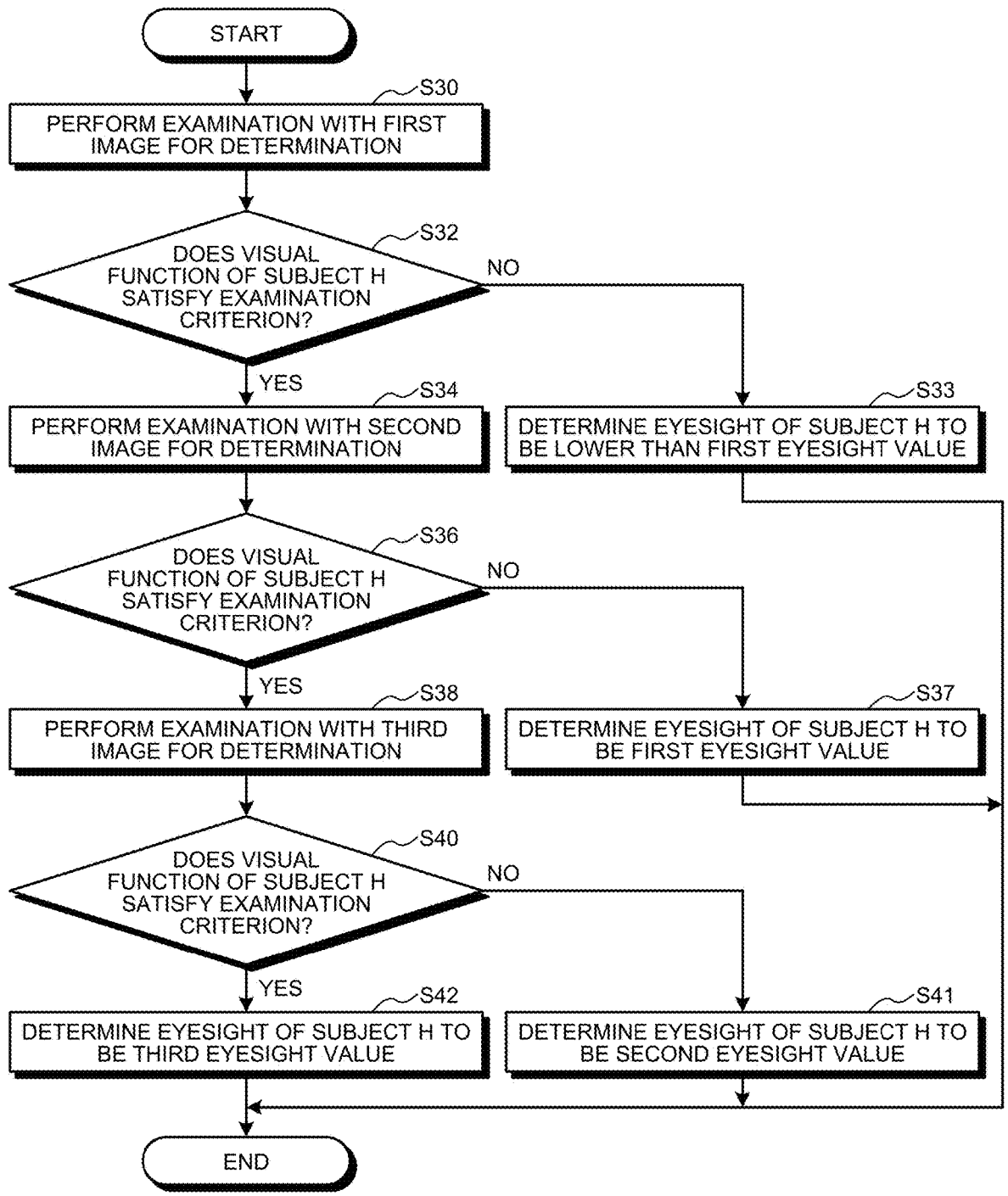
FIG. 17 is a flowchart illustrating an exemplary case in which the eyesight of a test subject is detected.

The visual function detection apparatus 100 displays the image 231 for determination with different patterns to detect the degree of the visual function of the test subject H step by step. The following describes the method. FIG. 17 is a flowchart illustrating an exemplary case in which the eyesight of the test subject is detected. As illustrated in FIG. 17, the visual function detection apparatus 100 first performs an examination with a first image for determination (Step S30). The first image for determination is an image, in which the area of the first images 241 and the second images 242 is larger among the image 231 for determination with a plurality of patterns, and is the image 231A for determination illustrated in FIG. 10 in the example of the present embodiment. The visual function detection apparatus 100, at Step S30, executes the examination illustrated in FIG. 13 using this first image for determination (the image 231A for determination). That is, in this case, the visual function detection apparatus 100 displays the first image for determination (the image 231A for determination) at the first position P1 and the second position P2 to determine whether the visual function of the test subject H satisfies the examination criterion.

When determining that the visual function of the test subject H does not satisfy the examination criterion by the examination with the first image for determination (No at Step S32), the visual function detection apparatus 100 determines the eyesight of the test subject H to be lower than a first eyesight value (Step S33), and ends the present processing. The first eyesight value is an eyesight when it is determined that the visual function of the test subject H satisfies the examination criterion of the first image for determination, and is 0.3, for example. However, the value of the first eyesight value is set depending on the shape of the first image for determination, i.e., the size of the first images 241 and the second images 242.

When determining that the visual function of the test subject H satisfies the examination criterion by the examination with the first image for determination (Yes at Step S32), the visual function detection apparatus 100 performs an examination with a second image for determination (Step S34). The second image for determination is an image smaller in the area of the first images 241 and the second images 242 than the first image for determination, and is the image 231B for determination illustrated in FIG. 11 in the example of the present embodiment. The visual function detection apparatus 100, at Step S34, executes the examination illustrated in FIG. 13 using this second image for determination (the image 231B for determination) to determine whether the visual function of the test subject H satisfies the examination criterion.

When determining that the visual function of the test subject H does not satisfy the examination criterion by the examination with the second image for determination (No at Step S36), the visual function detection apparatus 100 determines the eyesight of the test subject H to be the first eyesight value (Step S37), and ends the present processing. When determining that the visual function of the test subject H satisfies the examination criterion by the examination with the second image for determination (Yes at Step S36), the visual function detection apparatus 100 performs an examination with a third image for determination (Step S38). The third image for determination is an image smaller in the area of the first images 241 and the second images 242 than the second image for determination, and is the image 231C for determination illustrated in FIG. 12 in the example of the present embodiment. The visual function detection apparatus 100, at Step S38, executes the examination illustrated in FIG. 13 using this third image for determination (the image 231C for determination) to determine whether the visual function of the test subject H satisfies the examination criterion.

When determining that the visual function of the test subject H does not satisfy the examination criterion by the examination with the third image for determination (No at Step S40), the visual function detection apparatus 100 determines the eyesight of the test subject H to be a second eyesight value (Step S41), and ends the present processing. The second eyesight value is an eyesight when it is determined that the visual function of the test subject H satisfies the examination criterion of the second image for determination, and is a value larger than the first eyesight value. The second eyesight value is 0.5, for example. However, the value of the second eyesight value is set depending on the shape of the second image for determination, i.e., the size of the first images 241 and the second images 242.

When determining that the visual function of the test subject H satisfies the examination criterion by the examination with the third image for determination (Yes at Step S40), the visual function detection apparatus 100 determines the eyesight of the test subject H to be a third eyesight value (Step S42), and ends the present processing. The third eyesight value is an eyesight when it is determined that the visual function of the test subject H satisfies the examination criterion of the third image for determination, and is a value larger than the second eyesight value. The third eyesight value is 1.0, for example. However, the value of the third eyesight value is set depending on the shape of the third image for determination, i.e., the size of the first images 241 and the second images 242. The visual function detector 220 derives information thus determined to be the eyesight values (the first eyesight value, the second eyesight value, and the third eyesight value) as information as a criterion for detecting eyesight as the visual function and stores the information in the storage unit 222, for example.

In the present embodiment, the first position P1 and the second position P2 are randomly determined. As a result, there is a high possibility that a position change pattern is different. Consequently, in this case, the test subject H is prevented from memorizing a pattern, and contingency can be eliminated more favorably. When the step-by-step examinations are thus performed, a pattern and an initial value for movement from the first position P1 to the second position P2 are preferably varied for each step. That is, the position change pattern is preferably varied as in a case in which when the first position P1 is at the lower left, whereas the second position P2 is at the upper right in the first image for determination, the first position P1 is at the upper left, whereas the second position P2 is at the lower left in the second image for determination. The visual function detection apparatus 100 may set a plurality of initial positions and position change patterns and select the initial position and the change pattern for each step, for example. When performing a next step examination, the visual function detection apparatus 100 selects the initial position and the change pattern from other than the initial position and the change pattern selected in a previous step examination.

In the example in FIG. 17, when the visual function of the test subject H satisfies the examination criterion of the third image for determination, the eyesight value is determined to end the processing. However, when the image 231 for determination as a higher examination criterion is present, the processing may be continued. Examples of the image 231 for determination as a higher examination criterion include an image smaller in the size of the first images 241 and the second images 242 than the third image for determination. However, the image 231 for determination as a higher examination criterion may be the image 231 for determination smaller in contrast than the third image for determination.

Figure 18:
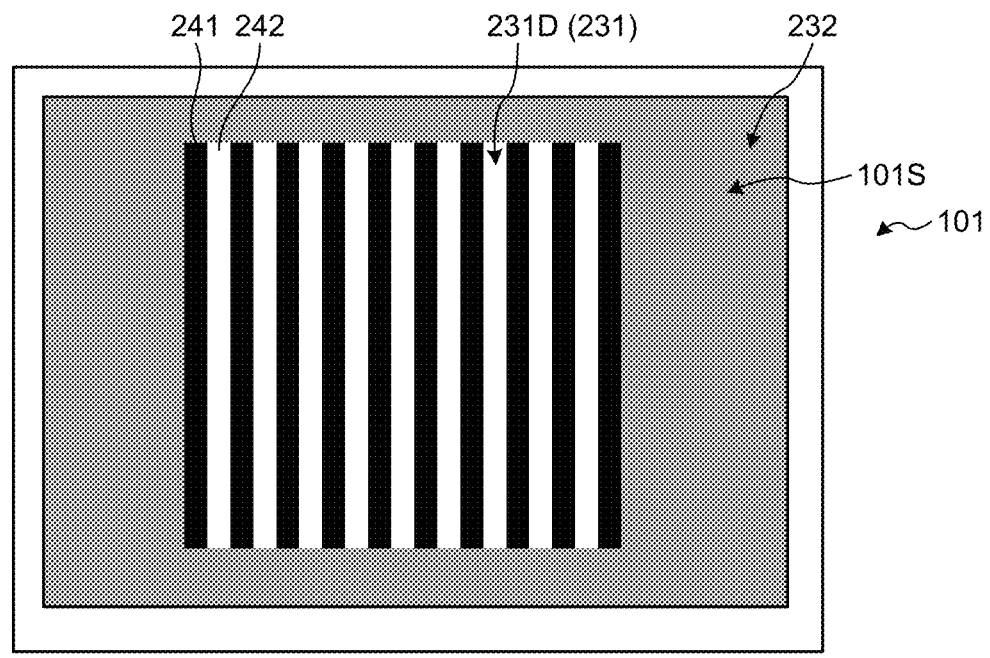
FIG. 18 is a diagram illustrating an example of the image for determination with a different contrast.
Figure 19:
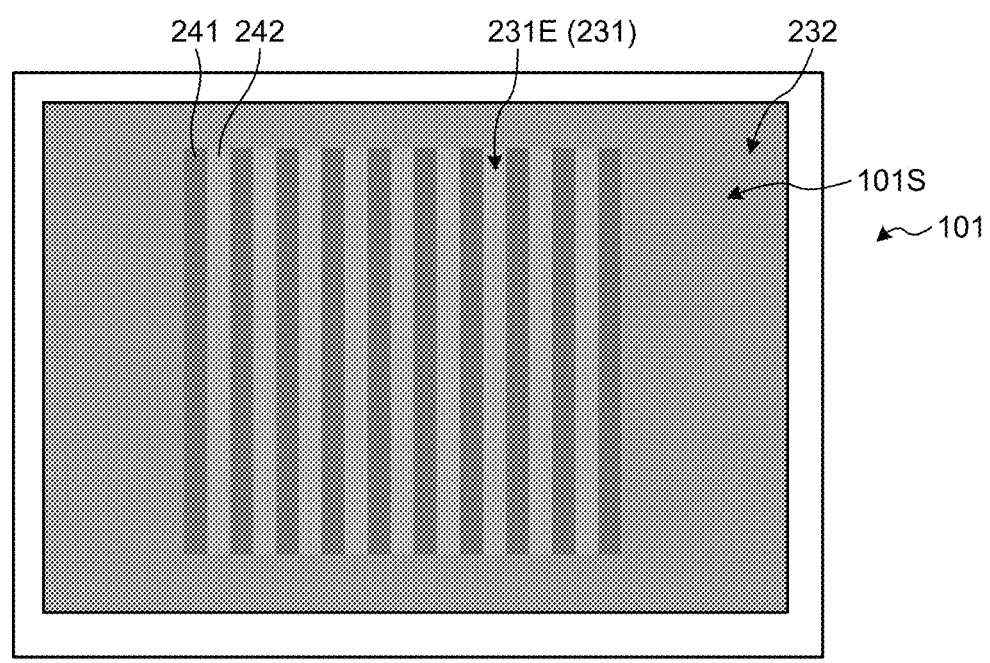
FIG. 19 is a diagram illustrating an example of the image for determination with a different contrast.

FIG. 18 and FIG. 19 are diagrams illustrating examples of the image for determination with different contrasts. The contrast referred to here is the degree of a luminance difference between maximum luminance and minimum luminance within the image 231 for determination. A larger degree of the luminance difference between the maximum luminance and the minimum luminance gives a larger contrast, whereas a smaller degree of the luminance difference between the maximum luminance and the minimum luminance gives a smaller contrast. The contrast is a value obtained by dividing the luminance of a pixel having maximum luminance among pixels within the image 231 for determination, i.e., the maximum luminance by the luminance of a pixel having minimum luminance among the pixels within the image 231 for determination, i.e., the minimum luminance, for example.

An image 231D for determination illustrated in FIG. 18 and an image 231E for determination illustrated in FIG. 19 are equal to each other in the size of the first images 241 and the second images 242. However, the image 231E for determination illustrated in FIG. 19 is smaller in contrast than the image 231D for determination illustrated in FIG. 18. That is, the image 231E for determination is smaller in the degree of the luminance difference between the maximum luminance and the minimum luminance than the image 231D for determination. Consequently, the image 231E for determination is more difficult for the test subject H to visually recognize than the image 231D for determination. In the present embodiment, the second images 242 have the maximum luminance, whereas the first images 241 have the minimum luminance. A smaller contrast gives a smaller luminance difference between the first images 241 and the second images 242, thus making it difficult for the test subject to visually recognize the image 231 for determination.

Thus, step-by-step examinations can be performed also by varying the contrast of the image 231 for determination. The visual function detection apparatus 100 may perform an examination using only the image 231 for determination varied in the size of the first images 241 and the second images 242, may perform an examination using only the image 231 for determination varied in contrast, or may use both of them or combine them with each other.

As described above, the visual function detection apparatus 100 according to the present embodiment includes: the display controller 216 that displays the image 231 for determination on the display screen 101S of the display unit (the display apparatus 101); the gazing point detector 214 that detects the position of the gazing point on the display screen 101S of the test subject H observing the display screen 101S; the positional relation detector 218 that detects the positional relation between the position of the image 231 for determination on the display screen 101S and the position of the gazing point; and the visual function detector 220 that detects the visual function of the test subject H based on the positional relation. The visual function detection apparatus 100 displays the image 231 for determination that attracts the attention of the test subject H to guide the line of sight of the test subject H to the image 231 for determination when the test subject H can visually recognize the image 231 for determination. The line of sight of the test subject is detected as the gazing point, and based on the position of the gazing point and the position of the image 231 for determination, whether the test subject H can visually recognize the image 231 for determination is determined to detect the visual function of the test subject H. Consequently, the visual function detection apparatus 100 eliminates the need for self-declaration about whether the test subject H can visually recognize the image 231 for determination, can appropriately detect the gazing point, and can appropriately determine whether the test subject H can visually recognize the image 231 for determination based on the gazing point. Consequently, the visual function detection apparatus 100 can appropriately examine the visual function of the test subject H.

The display controller 216 displays the image 231 for determination at the first position P1 on the display screen 101S and then displays the image 231 for determination at a position different from the first position P1 on the display screen 101S (the second position P2). The visual function detector 220 detects the visual function of the test subject H based on the positional relation at the first position P1 and the positional relation at the position different from the first position P1. The visual function detection apparatus 100 detects the positional relation for each position to perform determination and can thereby reduce contingency and appropriately examine the visual function of the test subject H.

The display controller 216 displays the first images 241 and the second images 242 different from each other in luminance as the image 231 for determination within the display region 101T. This visual function detection apparatus 100 displays the first images 241 and the second images 242 different from each other in luminance as the image 231 for determination, and can thereby, when the test subject H can visually recognize the image 231 for determination, appropriately guide the line of sight and appropriately examine the visual function.

The display controller 216 displays the first images 241 and the second images 242 within the display region 101T and displays a plurality of types of the images 231 for determination different from each other in the size of the first images 241 and the second images 242 at different timings. The visual function detector 220 detects the visual function of the test subject H based on the positional relation for each of the types of the images 231 for determination. This visual function detection apparatus 100 performs an examination for each of the types of the images 231 for determination and can thereby evaluate the visual function step by step.

The display controller 216 displays the image 232 for background in the region other than the display region 101T on the display screen 101S, and makes the average luminance of the image 231 for determination match the average luminance of the image 232 for background. This visual function detection apparatus 100 makes the average luminance of the image 231 for determination and that of the image 232 for background match each other to prevent false determination that the test subject H can visually recognize the image 231 for determination when the test subject H directs the line of sight to the image 231 for determination due to a luminance difference, although the test subject H cannot visually recognize the image 231 for determination itself. Consequently, the visual function detection apparatus 100 can appropriately evaluate the visual function.

The display controller 216 displays a plurality of types of the images 231 for determination different from each other in contrast at different timings, and the visual function detector 220 detects the visual function of the test subject H based on the positional relation for each of the types of the images 231 for determination. This visual function detection apparatus 100 performs an examination for each of the types of the images 231 for determination different from each other in contrast and can thus evaluate the visual function step by step.

The visual function detector 220 detects the visual function of the test subject H based on whether the position of the gazing point is present within the display region 101T. This visual function detection apparatus 100 thus performs detection of the visual function and can thus evaluate the visual function with high accuracy.

The gazing point detector 214 detects the gazing point a plurality of times while the image 231 for determination is displayed. The visual function detector 220 determines that the test subject H can visually recognize the image 231 for determination when the number of times the position of the gazing point is present within the display region 101T is equal to or more than a threshold set in advance. This visual function detection apparatus 100 thus performs detection of the visual function and can thus evaluate the visual function with high accuracy.

Figure 20:
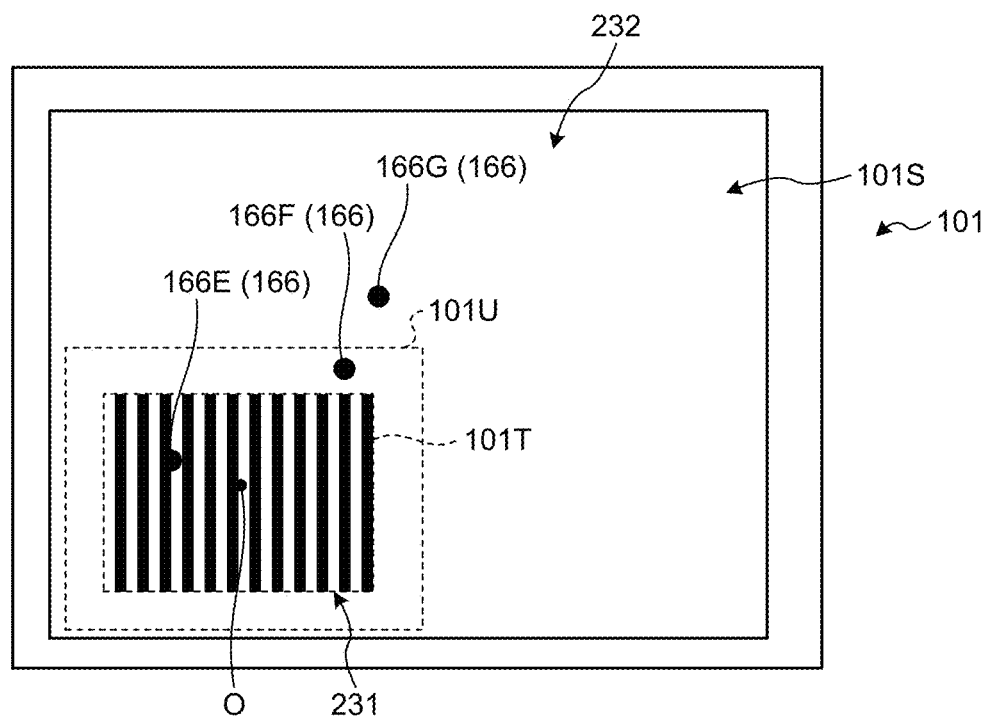
FIG. 20 is a diagram illustrating another example of detection of effective gazing points.

FIG. 20 is diagram illustrating another example of detection of the effective gazing points. In the present embodiment, determination about whether the visual function of the test subject H satisfies the examination criterion is performed based on whether the number of the effective gazing points is equal to or more than the threshold. As to the effective gazing points, the gazing points present within the display region 101T are detected as the effective gazing points. However, the method of detecting the effective gazing points is not limited to this example. As illustrated in FIG. 20, for example, the positional relation detector 218 may also detect the gazing point present within an effective region 101U as the effective gazing points. The effective region 101U is a region on the display screen 101S overlapping with the entire region of the display region 101T and is a region larger in area than the display region 101T. In the example in FIG. 20, a gazing point 166E is the gazing point 166 present within the display region 101T, whereas a gazing point 166F is the gazing point present outside the display region 101T and within the effective region 101U. A gazing point 166G is the gazing point present outside the effective region 101U. In this case, the positional relation detector 218 defines the gazing point 166E and the gazing point 166F as the effective gazing points and does not define the gazing point 166G as the effective gazing points. Thus, detection of the visual function can appropriately be performed also when the test subject H visually recognizes the image 231 for determination simply with a slightly deviated point of view.

The effective region 101U in this case is determined to be larger in area by a certain amount than the display region 101T. This certain amount can be set to any amount. The effective region 101U may be set based on a distance from a central point O of the display region 101T.

The visual function detector 220 may perform weighting on the effective gazing points. That is, when determining that the visual function of the test subject H satisfies the examination criterion, the visual function detector 220 may set the weight of the gazing point 166F to be smaller than that of the gazing point 166E. Weighting is thus performed, whereby detection of the visual function can be performed more appropriately. The visual function detector 220 may calculate a value obtained by multiplying the total number of the gazing point 166F by a coefficient k1 that is smaller than 1, and define a value obtained by adding the total number of the gazing point 166E to the value as the number of the effective gazing points, for example. Conversely, the visual function detector 220 may calculate a value obtained by multiplying the total number of the gazing point 166E by a coefficient k2 that is larger than 1, and define a value obtained by adding the total number of the gazing point 166F to the value as the number of the effective gazing points. Further, both of these coefficients k1 and k2 may be used.

The visual function detector 220 may perform weighting such that the weight of the effective gazing point detected as the gazing point 166 at an earlier timing is larger. The visual function detector 220 may multiply the total number of the effective gazing points detected as the gazing point 166 at an earlier timing than a certain time by the coefficient k2 that is larger than 1, multiply the total number of the effective gazing points detected as the gazing point 166 at a later timing than the certain time by the coefficient k1 that is smaller than 1, or combine these with each other, for example. The effective gazing point at a later timing may be given a smaller value of the coefficient to be multiplied. Even when gazing at the image 231 for determination at a timing when it is displayed, the test subject H may then move the line of sight. In such a case, the weight of the effective gazing point at an earlier timing is made larger, whereby even when the test subject H can visually recognize the image 231 for determination but then moves the line of sight, determination that the test subject H can visually recognize the image 231 for determination can be performed more favorably.

The visual function detector 220 may perform weighting such that the weight of the effective gazing point detected as the gazing point 166 at an earlier timing is smaller. That is, in a period shortly after the image 231 for determination is displayed, there may be a possibility that the reaction of the test subject H delays. Thus, with the weighting, determination that the test subject H can visually recognize the image 231 for determination can be performed more favorably. Such a way of temporal weighting can be set as appropriate in accordance with a situation.

Figure 21:
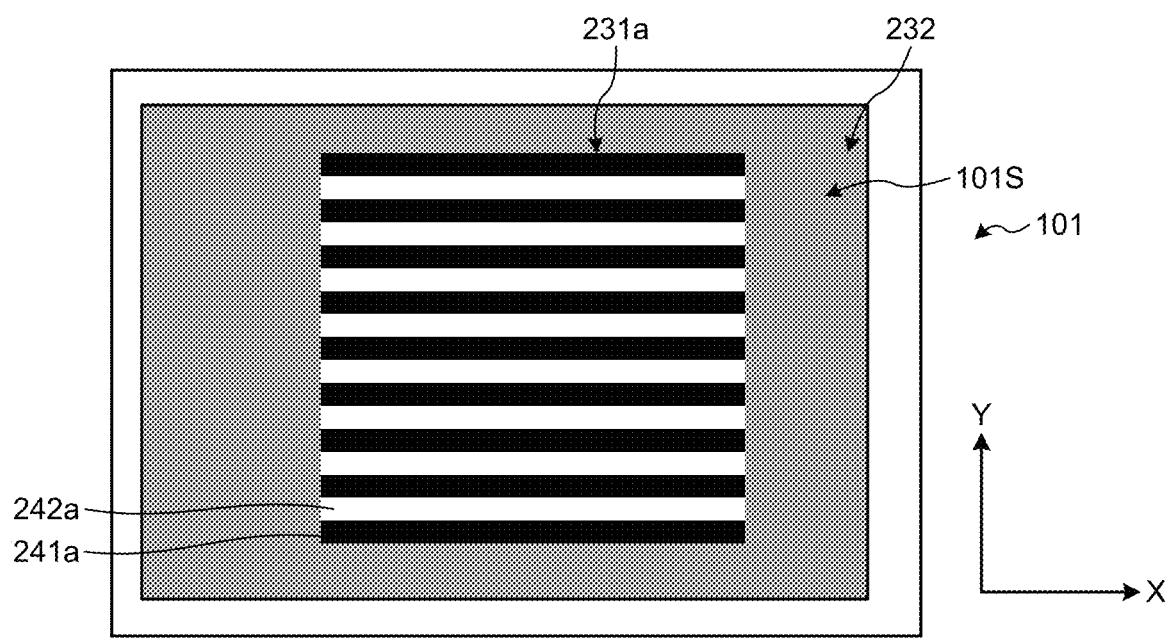
FIG. 21 is a diagram illustrating another example of the image for determination.
Figure 22:
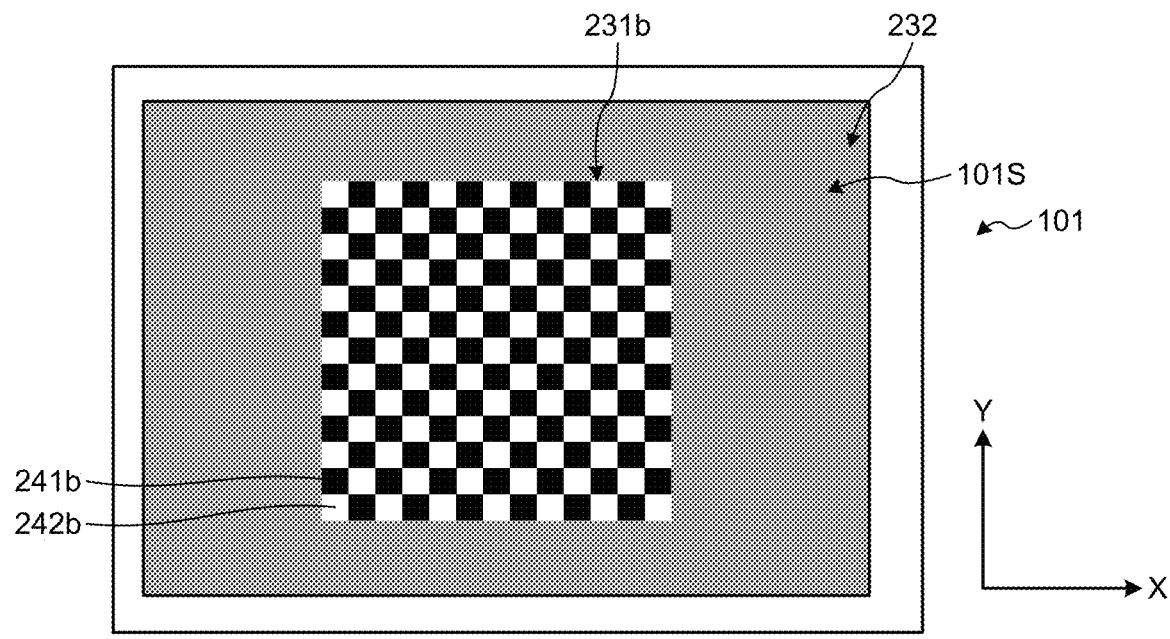
FIG. 22 is a diagram illustrating another example of the image for determination.
Figure 23:
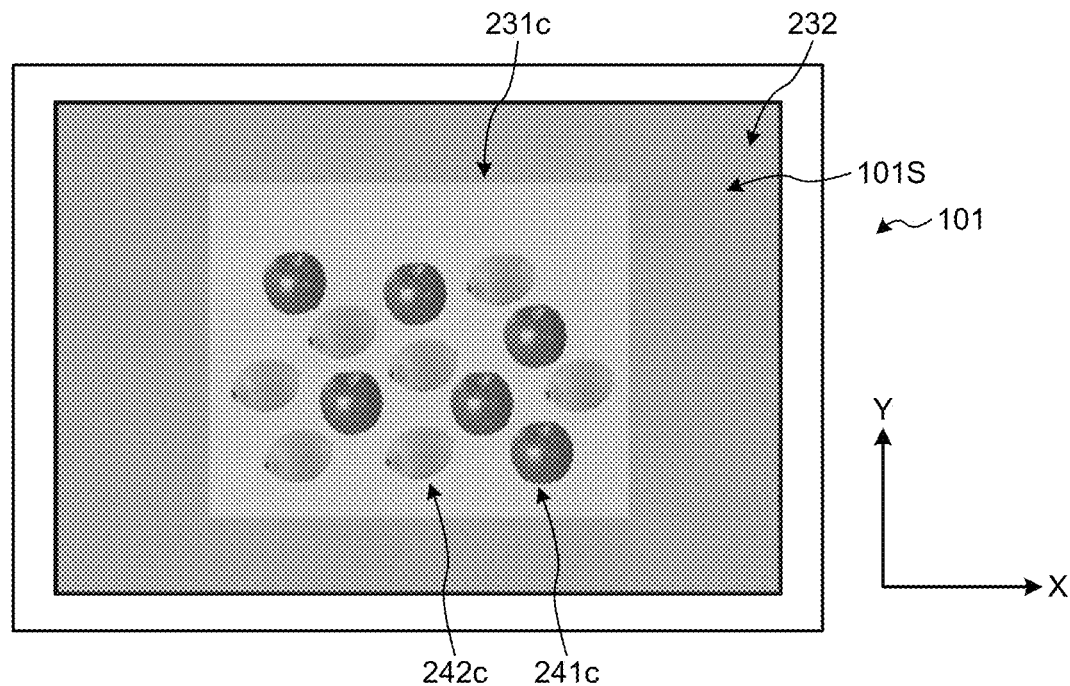
FIG. 23 is a diagram illustrating another example of the image for determination.

FIG. 21 to FIG. 23 are diagrams each illustrating another example of the image for determination. While the image 231 for determination of the present embodiment has a stripe shape in which the first images 241 and the second images 242 are alternately arranged along the X-axial direction, display of the image 231 for determination is not limited to this example. As illustrated in an image 231a for determination in FIG. 21, for example, the image 231 for determination may have a stripe shape in which first images 241a and second images 242a are alternately arranged along the Y-axial direction. As illustrated in an image 231b for determination in FIG. 22, the image 231 for determination may have a checkered pattern in which first images 241b and second images 242b are alternately arranged along the X-axial direction and the Y-axial direction. As illustrated in an image 231c for determination in FIG. 23, first images 241c and second images 242c may be images different from each other in luminance and shape. While in the example in FIG. 23, the first images 241c and the second images 242c are fruits, the images are not limited to fruits.

Second Embodiment (Visual Function Detection Apparatus)

The following describes a second embodiment. The contents of the second embodiment may be combined with the contents of the first embodiment. For parts in the second embodiment common to the first embodiment in configuration, a description thereof is omitted. The visual function detection apparatus 100 according to the second embodiment has structures similar to those described based on FIG. 1 to FIG. 12 of the first embodiment and executes similar processing.

Like the first embodiment, when the visual function detection is performed, the display controller 216 displays the image 231 for determination and the image 232 for background on the display screen 101S of the display apparatus 101. During the visual function detection, the test subject H observes the display screen 101S, and the gazing point detector 214 detects the gazing point 166 of the test subject H at that time. The positional relation detector 218 detects a positional relation indicating a relation between the position of the image 231 for determination on the display screen 101S and the position of the gazing point detected by the gazing point detector 214, and the visual function detector 220 detects the visual function of the test subject H based on a detection result of the positional relation. The following describes the flow detecting the visual function.

Figure 24:
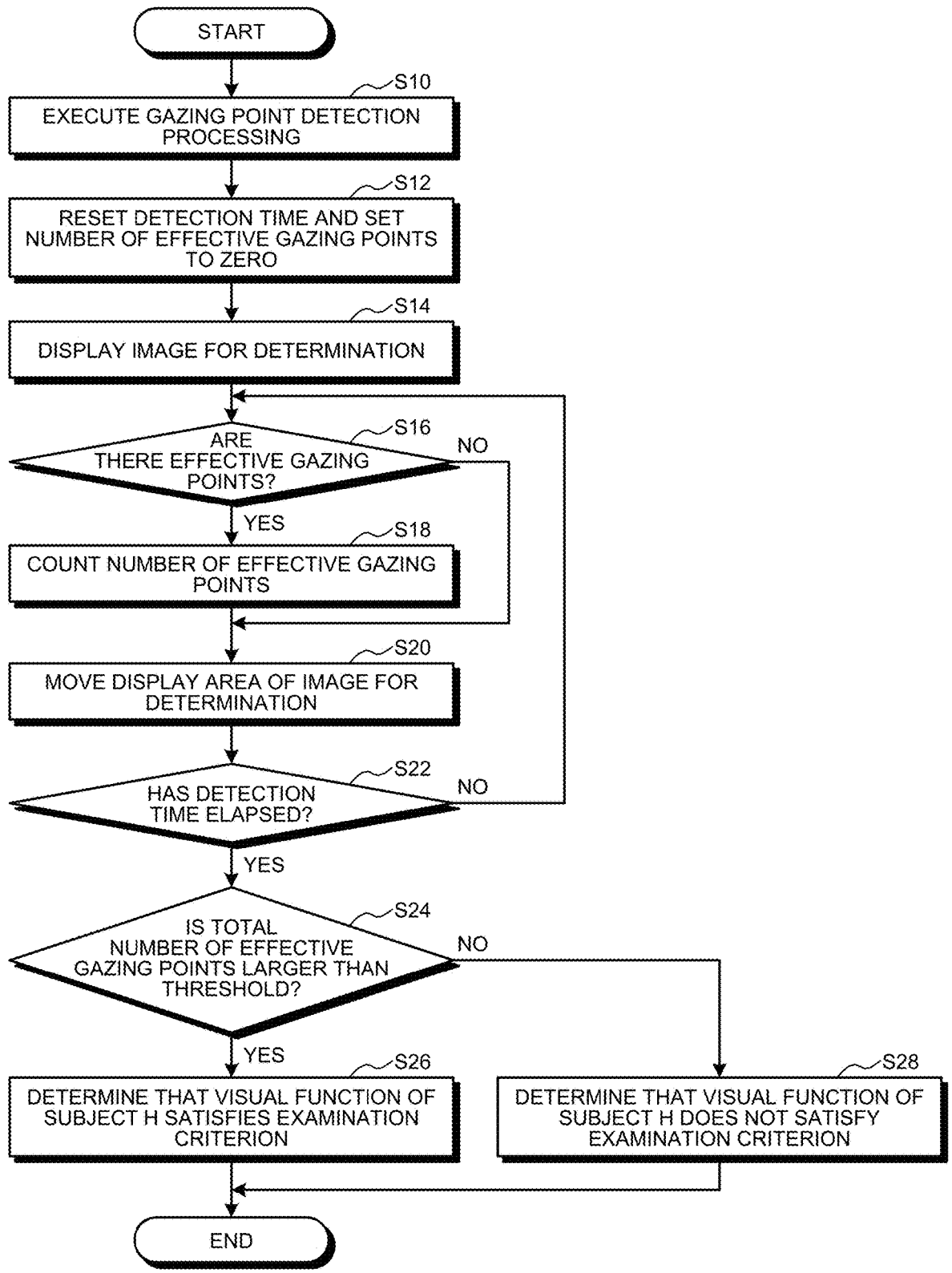
FIG. 24 is a flowchart illustrating the flow of detecting a visual function.
Figure 25:
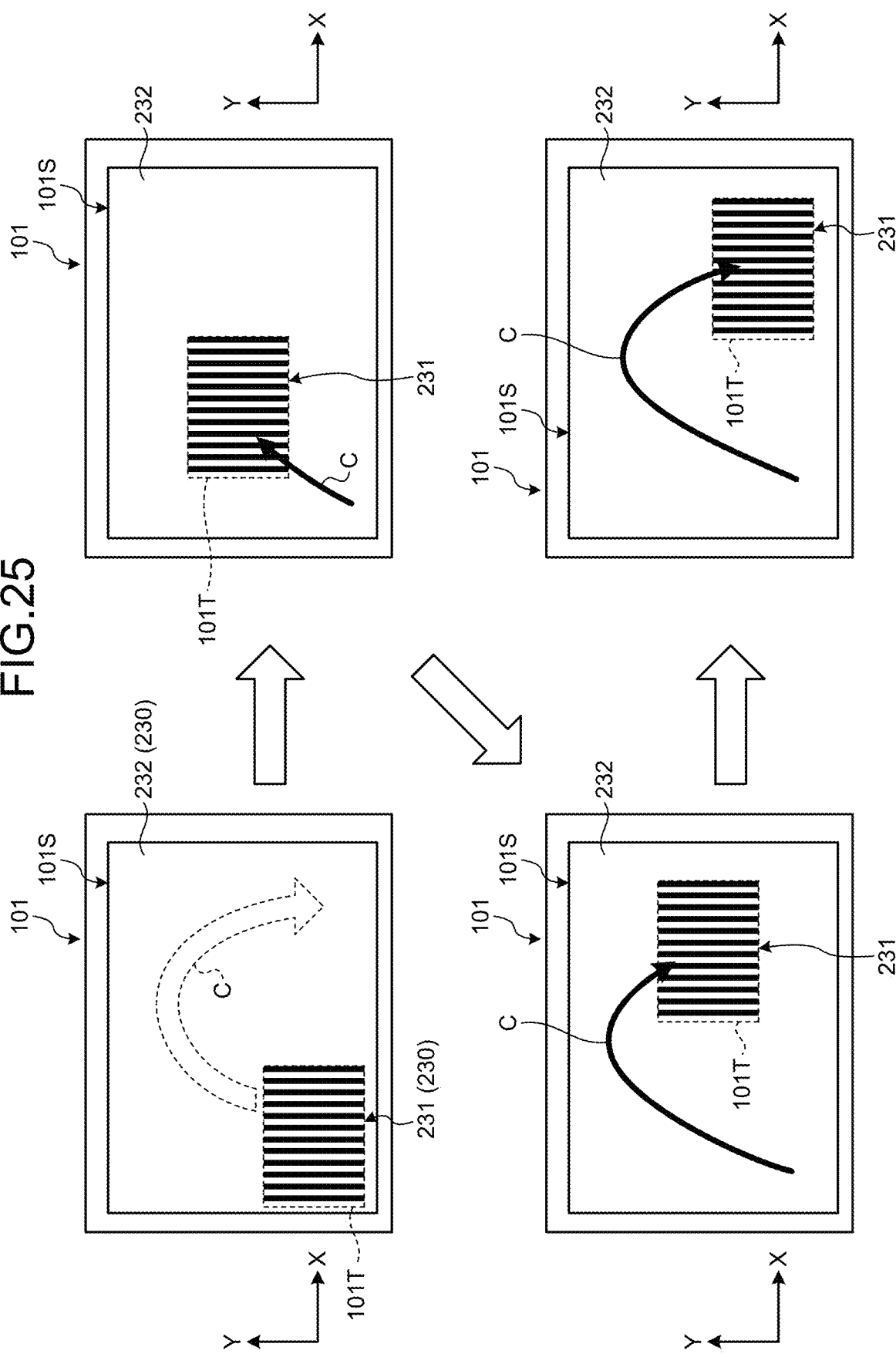
FIG. 25 is a diagram illustrating movement of the image for determination.

FIG. 24 is a flowchart illustrating the flow of detecting the visual function. FIG. 25 is a diagram for illustrating movement of the image for determination. As illustrated in FIG. 24, when the visual function detection is performed, the visual function detection apparatus 100 executes the gazing point detection processing described above by the gazing point detector 214 (Step S10) to start detection of the position of the gazing point 166 of the test subject H positioned in front of the display screen 101S. The image data of the eyeball 111 of the test subject is acquired every certain time by photographing by the image data acquisition unit 206. Consequently, the gazing point detector 214 detects the position of the gazing point 166 every certain time. This certain time is about 1/60 second, for example, and thus the gazing point 166 is detected about 60 times per second. However, this certain time has any duration. The gazing point detector 214 continues position detection of the gazing point 166 over a period during which the image 231 for determination is displayed described below.

The visual function detection apparatus 100 then resets a detection time and sets the number of the effective gazing points to zero (Step S12), and displays the image 231 for determination by the display controller 216 (Step S14). The detection time is a time set in advance and is a period during which the image 231 for determination is displayed to perform gazing point detection. The visual function detection apparatus 100 resets the detection time, starts display of the image 231 for determination and the gazing point detection, and starts to count a time from the timing of the start. The effective gazing points indicate the gazing point 166 determined to be present within the display region 101T of the image 231 for determination and will be described below in detail. The visual function detection apparatus 100 sets the number of the effective gazing points to zero and starts to count the effective gazing points. The detection time is about 3 seconds or more and 5 seconds or less, for example, which is not limiting, and can be set to any time.

The gazing point detector 214 performs detection of the gazing point 166 in a period during which the display controller 216 displays the image 231 for determination. The visual function detection apparatus 100 detects whether there are effective gazing points from the position data of the gazing point 166 detected by the gazing point detector 214 and the position data of the image 231 for determination (the display region 101T) on the display screen 101S by the positional relation detector 218 (Step S16). Specifically, the positional relation detector 218 detects whether within the display region 101T of the image 231 for determination displayed at a timing when the gazing point 166 is displayed, the gazing point 166 is positioned. When the gazing point 166 is positioned within the display region 101T at the timing when the gazing point 166 is detected, the positional relation detector 218 determines the gazing point 166 to be the effective gazing point. When the gazing point 166 is not positioned within the display region 101T at the timing when the gazing point 166 is detected, i.e., is positioned outside the display region 101T, the positional relation detector 218 determines the gazing point 166 not to be the effective gazing point. In other words, the positional relation detector 218 determines, among the gazing points 166 detected within the display period of the image 231 for determination at a certain position, the gazing point 166 positioned within the display region 101T of the image 231 for determination to be the effective gazing point. This determination about whether the gazing point 166 is the effective gazing point corresponds to detection of the positional relation.

When determining that there are gazing points (Yes at Step S16), the visual function detection apparatus 100 counts the number of the effective gazing points by the positional relation detector 218 (Step S18). That is, when determining that there are gazing points, the gazing point detector 214 adds the number of the gazing points 166 determined to be the effective gazing points to the number of the effective gazing points counted so far. That is, when the number of the effective gazing points is zero so far, if one effective gazing point is newly detected, the number of the effective gazing points is one.

After counting the number of the effective gazing points, the visual function detection apparatus 100 moves the display region 101T of the image 231 for determination (the image 231 for determination) by the display controller 216 (Step S20). When not determining that there are effective gazing points (No at Step S16), i.e., when determining that there is no effective gazing point, the visual function detection apparatus 100 also proceeds to Step S20 to move the display region 101T of the image 231 for determination. After moving the display region 101T, the visual function detection apparatus 100 determines whether the detection time has elapsed (Step S22). If the detection time has not elapsed (No at Step S22), the visual function detection apparatus 100 returns to Step S16 to repeat the subsequent processing. That is, the visual function detection apparatus 100 determines, among the gazing points 166 detected within the display period of the image 231 for determination at the destination of the movement, the gazing point 166 positioned within the display region 101T of the image 231 for determination to be the effective gazing point. The visual function detection apparatus 100 repeats the processing to detect the effective gazing points while moving the display region 101T until the detection time elapses.

The following describes an example in which the image 231 for determination, or the display region 101T in this example, is moved. FIG. 25 illustrates an example in which the display region 101T is moved along a trajectory C. The upper left drawing of FIG. 25 illustrates a state in which the display region 101T is at an initial position. That is, the display controller 216, at Step S14, sets the display region 101T at the position of the upper left drawing of FIG. 25, i.e., the initial position and displays the image 231 for determination at the position. The initial position is a position on the display screen 101S initially set as the display region 101T and is any set position. The display controller 216 displays the image 230 so as to position the display region 101T at the set initial position. Thus, the image 231 for determination out of the image 230 is displayed within the display region 101T positioned at the initial position, whereas the image 232 for background out of the image 230 is displayed outside the display region 101T.

The display controller 216 then gradually moves the display region 101T along the trajectory C for each frame, i.e., for each Step S20 until the detection time expires. The display controller 216 moves the display region 101T along the trajectory C while the image 231 for determination is displayed. Consequently, as illustrated in FIG. 25, the image 231 for determination continuously moves along the trajectory C. The continuous movement can also be referred to as movement of the position of the display region 101T for each frame.

The display controller 216 moves the display region 101T by a distance set in advance for each Step S20. This distance to be moved is preferably shorter than the length of the display region 101T itself. Thus, this prevents the image 231 for determination from appearing to switch, and the image 231 for determination is visually recognized such that it moves more smoothly. While the trajectory C illustrated in FIG. 25 heads toward the upper center from the lower left and then heads toward the lower right, the trajectory C can be set to any trajectory. The trajectory C may move only in the X-axial direction, move only in the Y-axial direction, or move in both the X-axial direction and the Y-axial direction such as circularly, for example. While in the present embodiment, the contents displayed by the image 231 for determination during the movement of the display region 101T do not change, the contents may change while the display region 101T moves.

A frame rate of the gazing point detection is preferably not smaller than a frame rate of the movement of the display region 101T. Thus, the gazing point detector 214 detects at least one for each position of the display region 101T even when the display region 101T is continuously moving. However, the frame rate of the gazing point detection may be not larger than the frame rate of the movement of the display region 101T.

Thus, the visual function detection apparatus 100 performs detection of the gazing point 166 while moving the display region 101T by leaving the image 231 for determination displayed until the detection time expires. The visual function detection apparatus 100 continues detection of the effective gazing points for each position of the display region 101T and continues to count the number of the detected effective gazing points until the detection time expires.

If the detection time elapses (Yes at Step S22), the visual function detection apparatus 100 performs determination of the visual function of the test subject H based on the positional relation, i.e., the detected effective gazing points by the visual function detector 220. Specifically, if the detection time elapses, the visual function detector 220 determines whether the total number of the effective gazing points for each position of the display region 101T is larger than a threshold set in advance (Step S24). If the total number of the effective gazing points is larger than the threshold (Yes at Step S24), the visual function detector 220 determines that the visual function of the test subject H satisfies the examination criterion (Step S26). On the other hand, if the total number of the effective gazing points is not larger than the threshold (No at Step S24), i.e., equal to or less than the threshold, the visual function detector 220 determines that the visual function of the test subject H does not satisfy the examination criterion (Step S28). With Step S26 or S28, the processing ends. The visual function detector 220 derives this determination result about whether the visual function of the test subject H satisfies the examination criterion as information as a criterion for detecting the visual function, and stores the information in the storage unit 222, for example.

Figure 26:
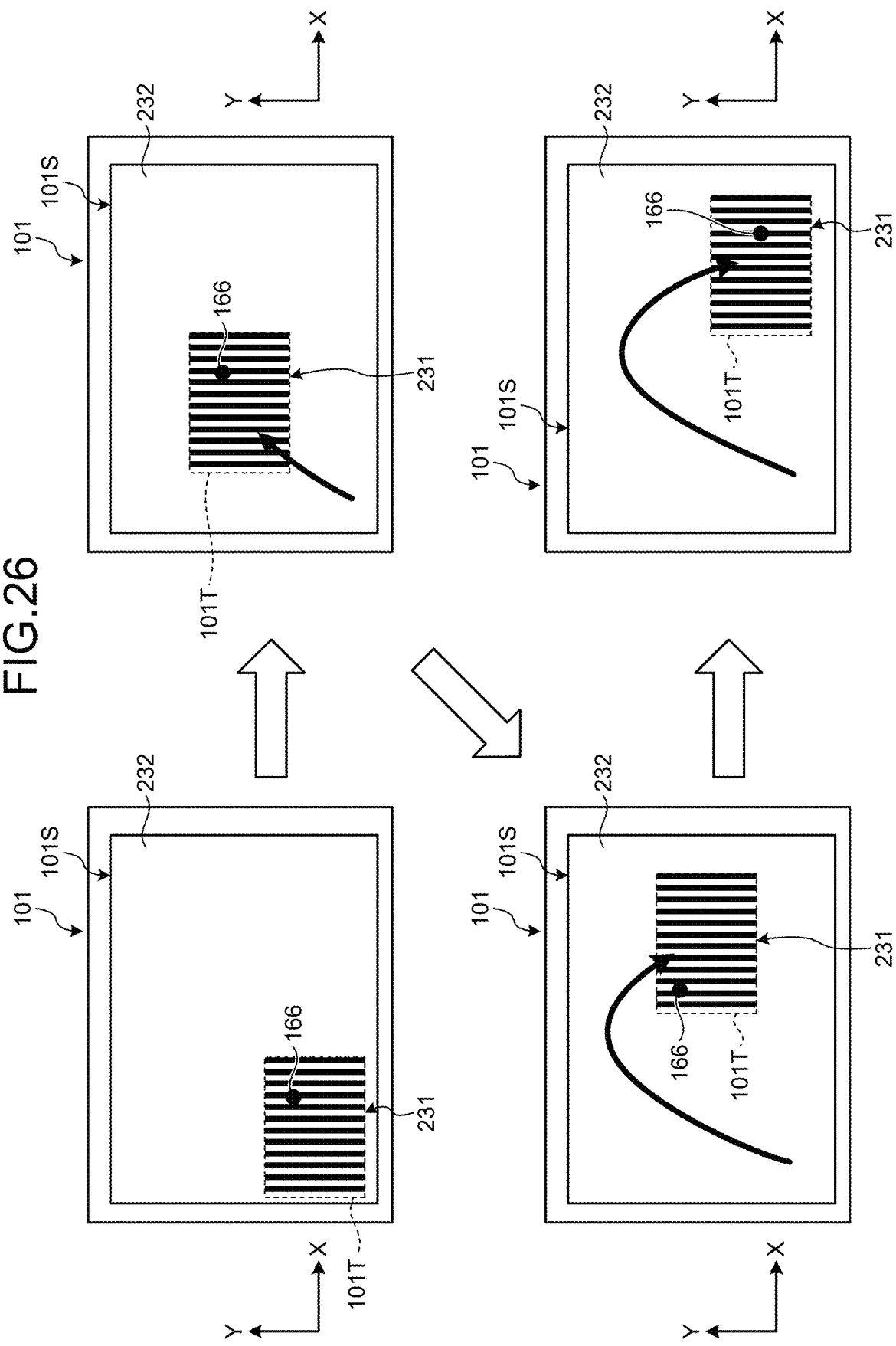
FIG. 26 is a diagram illustrating the positional relation between the gazing point and the image for determination.
Figure 27:
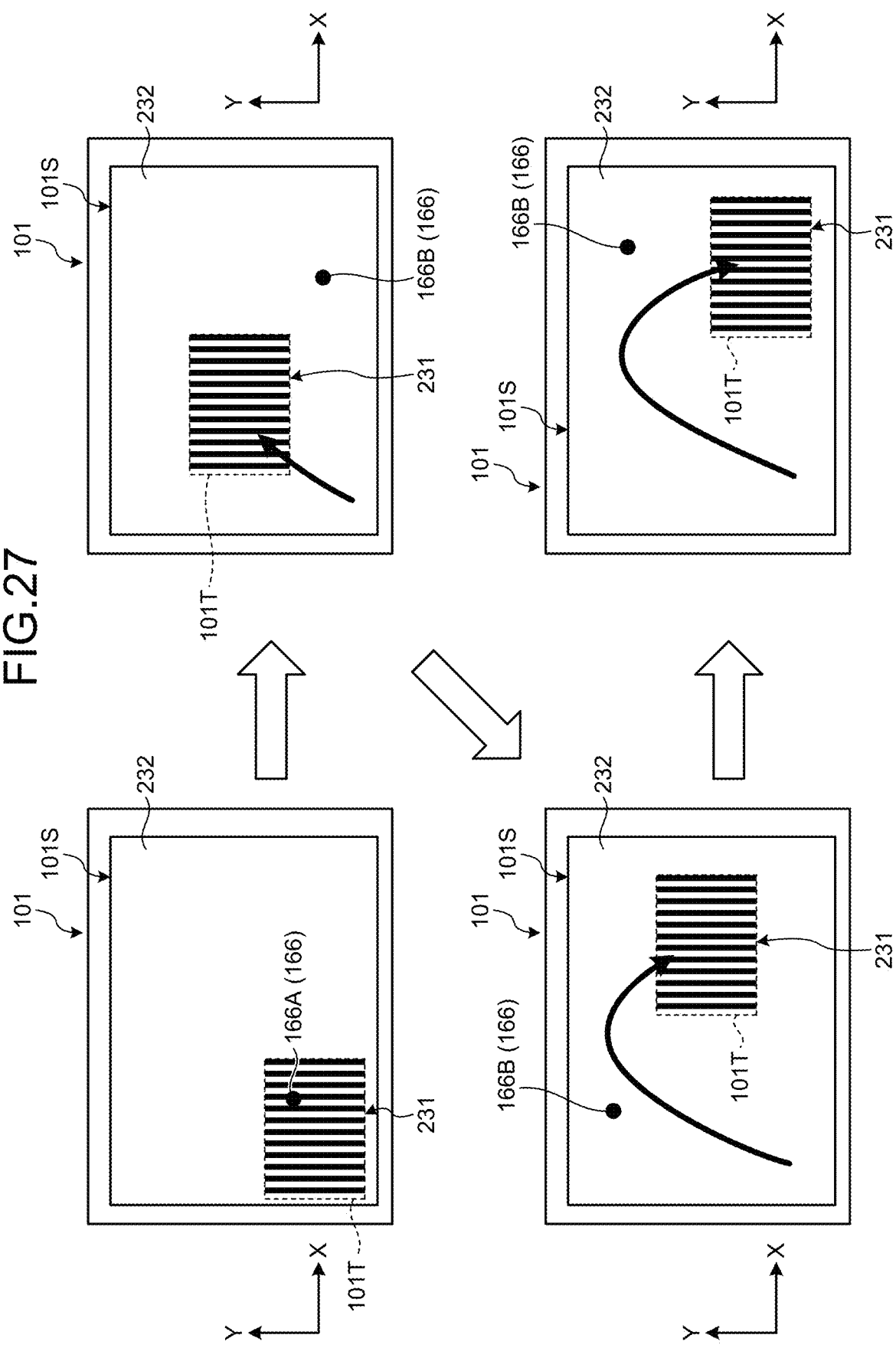
FIG. 27 is a diagram illustrating the positional relation between the gazing point and the image for determination.

FIG. 26 and FIG. 27 are diagrams each illustrating the positional relation between the gazing points and the image for determination. The image 231 for determination displayed on display screen 101S is an image that attracts attention of the test subject H. Consequently, when the test subject H can visually recognize the image 231 for determination, the test subject H directs the line of sight to the image 231 for determination. When the display region 101T of the image 231 for determination continuously moves, the line of sight of the test subject H moves while tracking the movement of the display region 101T. On the other hand, when the test subject H cannot visually recognize the image 231 for determination, the test subject H does not direct the line of sight to the image 231 for determination, and the line of sight of the test subject H does not track the movement of the display region 101T. In the present embodiment, using this tendency, based on the positional relation between the position of the gazing pint of the test subject H and the image 231 for determination, whether the test subject H can visually recognize the image 231 for determination is determined, whereby the visual function of the test subject H is detected.

In the example in FIG. 26, the gazing point 166 moves while tracking the movement of the display region 101T, and the number of the gazing points 166 positioned within the display region 101T, i.e., the number of the effective gazing points is larger. Consequently, in such a case, the visual function detector 220 determines that the test subject H can visually recognize the image 231 for determination and determines that the visual function of the test subject H satisfies the examination criterion. On the other hand, in the example in FIG. 27, the gazing point 166 does not track the movement of the display region 101T and varies, and the number of the gazing points 166 positioned within the display region 101T, i.e., the number of the effective gazing points is smaller. Consequently, the visual function detector 220 determines that the test subject H cannot visually recognize the image 231 for determination and determines that the visual function of the test subject H does not satisfy the examination criterion. The gazing point 166 at the upper right drawing of FIG. 27, for example, is positioned within the display region 101T at a different timing, i.e., the display region 101T at a timing when moved to the lower right drawing. However, the upper right gazing point 166 of FIG. 27, even if it is positioned within the display region 101T of the lower right drawing, is not positioned within the display region 101T of the upper right drawing, which is at the same timing. Thus, this upper right gazing point 166 is not determined to be positioned within the display region 101T, and is not determined to be the effective gazing point.

Even when the test subject H cannot visually recognize the image 231 for determination, the test subject H may gaze at a point in a concentrated manner, and there is a possibility that the gazing point is accidentally concentrated on the image 231 for determination. Given this situation, the visual function detection apparatus 100 according to the present embodiment displays the image 231 for determination while continuously moving the display region 101T, and detects the gazing point 166 at each timing. The visual function detection apparatus 100 thus continuously moves the position of the image 231 for determination to reduce contingency in which the gazing point is concentrated on the image 231 for determination even though the test subject H cannot visually recognize the image 231 for determination, and to improve visual function detection accuracy.

In the present embodiment, each time the display region 101T is moved, detection of the effective gazing points is performed. However, the positional relation detector 218 may perform detection of the effective gazing points collectively after a lapse of the detection time. In this case, the positional relation detector 218 acquires the position data of the gazing point 166 for each timing and the position data of the display region 101T for each timing. The positional relation detector 218 extracts the display region 101T and the gazing point 166 at the same timing and detects whether the gazing point 166 is positioned within the display region 101T. The positional relation detector 218 performs this detection for each gazing point 166 and can thereby collectively calculate the total number of the effective gazing points after a lapse of the detection time.

Figure 28:
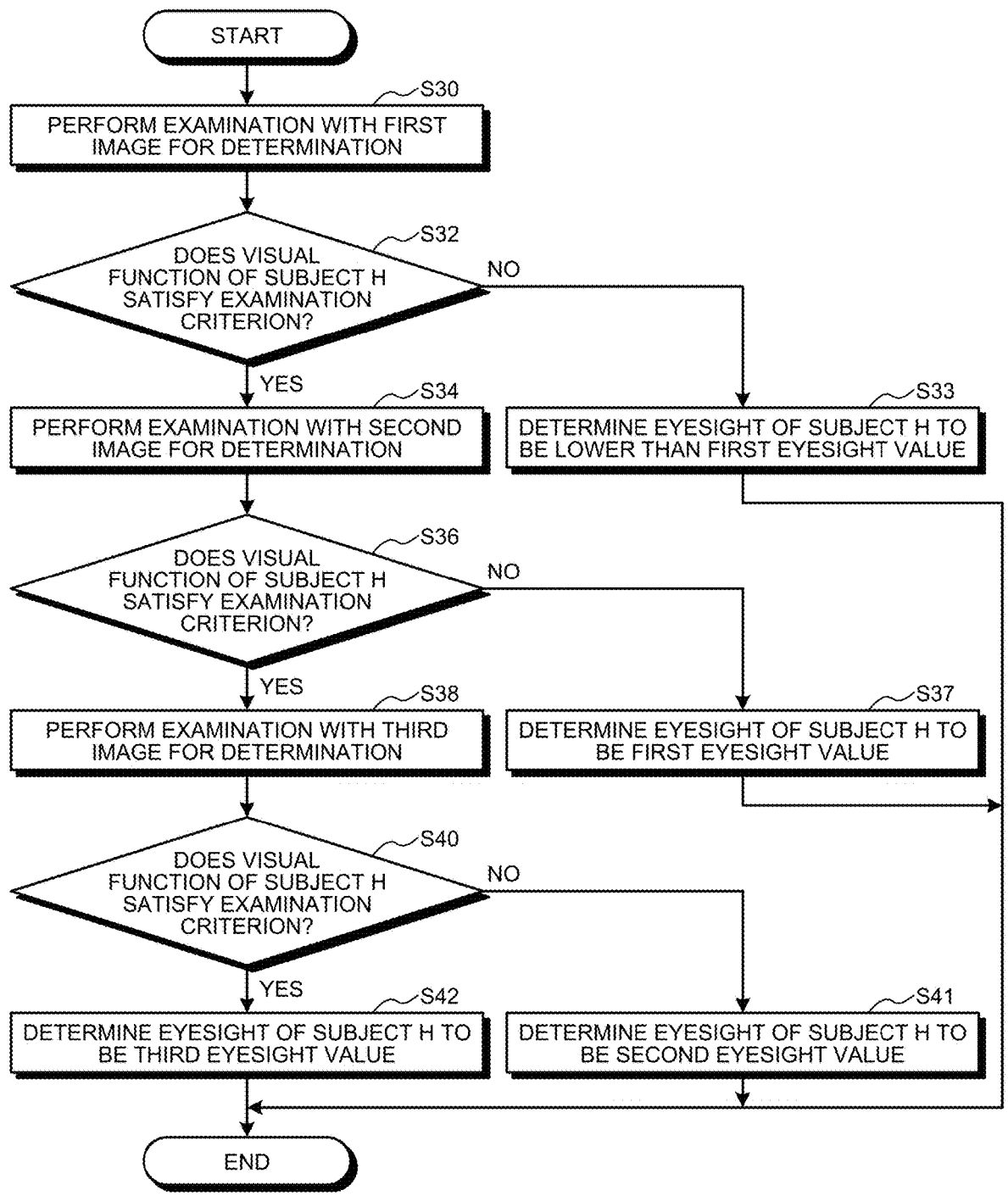
FIG. 28 is a flowchart illustrating an exemplary case in which the eyesight of the test subject is detected.

The visual function detection apparatus 100 displays the image 231 for determination with different patterns to detect the degree of the visual function of the test subject H step by step. The following describes the method. FIG. 28 is a flowchart illustrating an exemplary case in which the eyesight of the test subject is detected. As illustrated in FIG. 28, the visual function detection apparatus 100 first performs an examination with the first image for determination (Step S30). The first image for determination is an image in which the area of the first images 241 and the second images 242 is larger among the image 231 for determination with a plurality of patterns, and is the image 231A for determination illustrated in FIG. 33 in the example of the present embodiment. The visual function detection apparatus 100, at Step S30, executes the examination illustrated in FIG. 24 using this first image for determination (the image 231A for determination). That is, in this case, the visual function detection apparatus 100 displays the first image for determination (the image 231A for determination) to determine whether the visual function of the test subject H satisfies the examination criterion.

When determining that the visual function of the test subject H does not satisfy the examination criterion by the examination with the first image for determination (No at Step S32), the visual function detection apparatus 100 determines the eyesight of the test subject H to be lower than a first eyesight value (Step S33), and ends the present processing. The first eyesight value is an eyesight when it is determined that the visual function of the test subject H satisfies the examination criterion of the first image for determination, and is 0.3, for example. However, the value of the first eyesight value is set depending on the shape of the first image for determination, i.e., the size of the first images 241 and the second images 242.

When determining that the visual function of the test subject H satisfies the examination criterion by the examination with the first image for determination (Yes at Step S32), the visual function detection apparatus 100 performs an examination with a second image for determination (Step S34). The second image for determination is an image smaller in the area of the first images 241 and the second images 242 than the first image for determination, and is the image 231B for determination illustrated in FIG. 34 in the example of the present embodiment. The visual function detection apparatus 100, at Step S34, executes the examination illustrated in FIG. 24 using this second image for determination (the image 231B for determination) to determine whether the visual function of the test subject H satisfies the examination criterion.

When determining that the visual function of the test subject H does not satisfy the examination criterion by the examination with the second image for determination (No at Step S36), the visual function detection apparatus 100 determines the eyesight of the test subject H to be the first eyesight value (Step S37), and ends the present processing. When determining that the visual function of the test subject H satisfies the examination criterion by the examination with the second image for determination (Yes at Step S36), the visual function detection apparatus 100 performs an examination with a third image for determination (Step S38). The third image for determination is an image smaller in the area of the first images 241 and the second images 242 than the second image for determination, and is the image 231C for determination illustrated in FIG. 36 in the example of the present embodiment. The visual function detection apparatus 100, at Step S38, executes the examination illustrated in FIG. 24 using this third image for determination (the image 231C for determination) to determine whether the visual function of the test subject H satisfies the examination criterion.

When determining that the visual function of the test subject H does not satisfy the examination criterion by the examination with the third image for determination (No at Step S40), the visual function detection apparatus 100 determines the eyesight of the test subject H to be a second eyesight value (Step S41), and ends the present processing.

The second eyesight value is an eyesight when it is determined that the visual function of the test subject H satisfies the examination criterion of the second image for determination and is a value larger than the first eyesight value. The second eyesight value is 0.5, for example. However, the value of the second eyesight value is set depending on the shape of the second image for determination, i.e., the size of the first images 241 and the second images 242.

When determining that the visual function of the test subject H satisfies the examination criterion by the examination with the third image for determination (Yes at Step S40), the visual function detection apparatus 100 determines the eyesight of the test subject H to be a third eyesight value (Step S42), and ends the present processing. The third eyesight value is an eyesight when it is determined that the visual function of the test subject H satisfies the examination criterion of the third image for determination and is a value larger than the second eyesight value. The third eyesight value is 1.0, for example. However, the value of the third eyesight value is set depending on the shape of the third image for determination, i.e., the size of the first images 241 and the second images 242. The visual function detector 220 derives information determined to be the thus determined eyesight values (the first eyesight value, the second eyesight value, and the third eyesight value) as information as a criterion for detecting eyesight as the visual function and stores the information in the storage unit 222, for example.

When the step-by-step examinations are thus performed, the visual function detection apparatus 100 preferably varies the trajectory C and an initial position moving the display region 101T for each step. That is, the initial position and the trajectory C in the examination with the second image for determination are preferably varied relative to the initial position and the trajectory C in the examination with the first image for determination performed before. Thus, contingency can favorably be excluded. The visual function detection apparatus 100 may set a plurality of patterns of the initial position and the trajectory C, and may select the initial position and the trajectory C for each step, for example. When performing a next step examination, the visual function detection apparatus 100 selects the initial position and the trajectory C from those other than the initial position and the trajectory C selected in a previous step examination.

In the example in FIG. 28, upon the end of the examination with one image 231 for determination, the visual function detection apparatus 100 stops display of the image 231 for determination and starts the examination with the next image 231 for determination. However, the visual function detection apparatus 100 may continuously perform examinations with a plurality of the images 231 for determination. In this case, upon a lapse of the detection time at Step S22 in FIG. 24, the visual function detection apparatus 100 may return to Step S12, display another image 231 for display from the next frame, and perform an examination while moving the display region 101T in a similar manner. The visual function detection apparatus 100 may display the image 231A for determination for a duration of the detection time, and then switch to the image 231B for determination, for example, to continue a similar examination from the next frame, for example. The examinations are thus continuously performed, whereby the detection time can be reduced. Further, the visual function detection apparatus 100 can also display the image 231B for determination for a duration of the detection time and then switch to the image 231A for determination, for example, from the next frame, or can return, when an image for a certain eyesight cannot be visually recognized, to an examination with an image for a lower eyesight than the image.

While in the example in FIG. 28, when the visual function of the test subject H satisfies the examination result of the third image for determination, the eyesight value is determined and the processing ends, when the image 231 for determination as a higher examination criterion is present, the processing may be continued. Examples of the image 231 for determination as a higher examination criterion include an image smaller in the size of the first images 241 and the second images 242 than the third image for determination. However, the image 231 for determination as a higher examination criterion may be the image 231 for determination smaller in contrast than the third image for determination.

Figure 29:
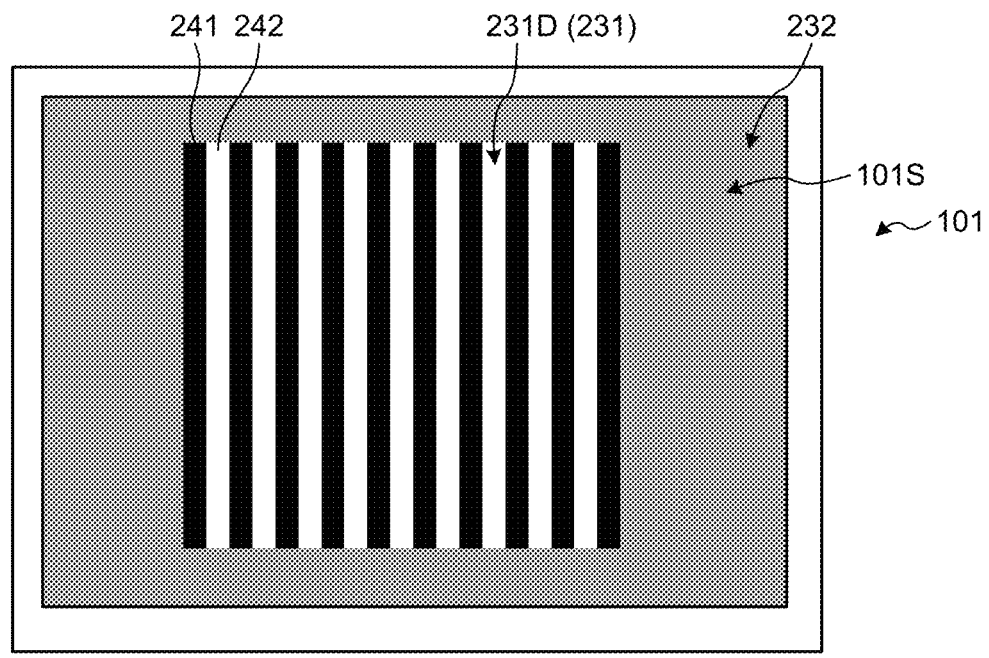
FIG. 29 is a diagram illustrating an example of the image for determination with a different contrast.
Figure 30:
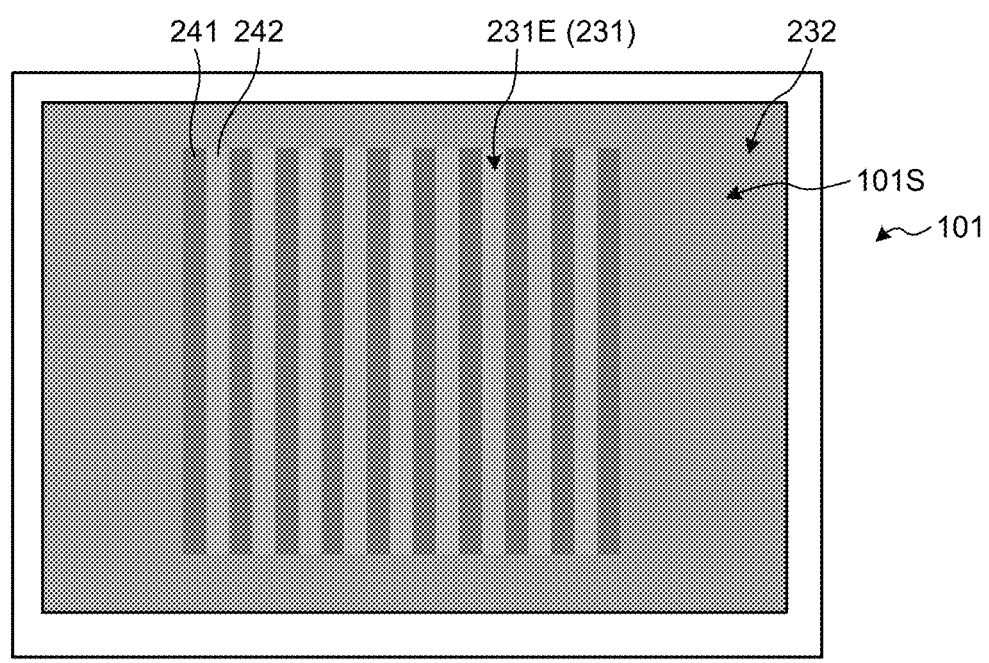
FIG. 30 is a diagram illustrating an example of the image for determination with a different contrast.

FIG. 29 and FIG. 30 are diagrams illustrating examples of the image for determination with different contrasts. The contrast referred to here is the degree of a luminance difference between maximum luminance and minimum luminance within the image 231 for determination. A larger degree of the luminance difference between the maximum luminance and the minimum luminance gives a larger contrast, whereas a smaller degree of the luminance difference between the maximum luminance and the minimum luminance gives a smaller contrast. The contrast is a value obtained by dividing the luminance of a pixel having maximum luminance among pixels within the image 231 for determination, i.e., the maximum luminance by the luminance of a pixel having minimum luminance among the pixels within the image 231 for determination, i.e., the minimum luminance, for example.

The image 231D for determination illustrated in FIG. 29 and the image 231E for determination illustrated in FIG. 30 are equal to each other in the size of the first images 241 and the second images 242. However, the image 231E for determination illustrated in FIG. 30 is smaller in contrast than the image 231D for determination illustrated in FIG. 29. That is, the image 231E for determination is smaller in the degree of the luminance difference between the maximum luminance and the minimum luminance than the image 231D for determination. Consequently, the image 231E for determination is more difficult for the test subject H to visually recognize than the image 231D for determination. In the present embodiment, the second images 242 have the maximum luminance, whereas the first images 241 have the minimum luminance. A smaller contrast gives a smaller luminance difference between the first images 241 and the second images 242, thus making it difficult for the test subject to visually recognize the image 231 for determination.

Thus, step-by-step examinations can be performed also by varying the contrast of the image 231 for determination. The visual function detection apparatus 100 may perform an examination using only the image 231 for determination varied in the size of the first images 241 and the second images 242, may perform an examination using only the image 231 for determination varied in contrast, or may use both of them or combine them with each other.

As described above, the visual function detection apparatus 100 according to the present embodiment has the display controller 216, the gazing point detector 214, the positional relation detector 218, and the visual function detector 220. The display controller 216 displays the image 231 for determination on the display screen 101S of the display unit (the display apparatus 101) and continuously moves the position of the image 231 for determination with the lapse of time while the image 231 for determination is displayed. The gazing point detector 214 detects the position of the gazing point of the test subject H observing the display screen 101S on the display screen 101S. The positional relation detector 218 detects the positional relation between the position of the image 231 for determination on the display screen 101S and the position of the gazing point. The visual function detector 220 detects the visual function of the test subject H based on the positional relation. This visual function detection apparatus 100 displays the image 231 for determination attracting the attention of the test subject H to guide the line of sight of the test subject H to the image 231 for determination when the test subject H can visually recognize the image 231 for determination. The visual function detection apparatus 100 detects the line of sight of the test subject as the gazing point, and based on the position of the gazing point and the position of the image 231 for determination, determines whether the test subject H can visually recognize the image 231 for determination, thus detects the visual function of the test subject H. Consequently, the visual function detection apparatus 100 eliminates the need for self-declaration about whether the test subject H can visually recognize the image 231 for determination, can appropriately detect the gazing point, and can appropriately determine whether the test subject H can visually recognize the image 231 for determination based on the gazing point. Consequently, the visual function detection apparatus 100 can appropriately examine the visual function of the test subject H.

Further, the visual function detection apparatus 100 continuously moves the position of the image 231 for determination while the image 231 for determination is displayed. Consequently, the visual function detection apparatus 100 can reduce the possibility of determining that the test subject H visually recognizes the image 231 for determination even though the test subject H cannot visually recognize the image 231 for determination, reduce contingency, and appropriately examine the visual function of the test subject H. In addition, the visual function detection apparatus 100 continuously moves the position of the display region 101T and can thus also examine the trackability of the line of sight of the test subject H.

The display controller 216 displays the first images 241 and the second images 242 different from each other in luminance as the image 231 for determination within the display region 101T. The visual function detection apparatus 100 displays the first images 241 and the second images 242 different from each other in luminance as the image 231 for determination, and can thereby, when the test subject H can visually recognize the image 231 for determination, appropriately guide the line of sight and appropriately examine the visual function.

The display controller 216 displays the first images 241 and the second images 242 within the display region 101T, and displays a plurality of types of the images 231 for determination different from each other in the size of the first images 241 and the second images 242 at different timings. The visual function detector 220 detects the visual function of the test subject H based on the positional relation for each of the types of the images 231 for determination. The visual function detection apparatus 100 performs an examination for each of the types of the images 231 for determination and can thereby evaluate the visual function step by step.

The display controller 216 displays the image 232 for background in the region other than the display region 101T on the display screen 101S, and makes the average luminance of the image 231 for determination match the average luminance of the image 232 for background. The visual function detection apparatus 100 makes the average luminance of the image 231 for determination and that of the image 232 for background match each other to prevent false determination that the test subject H can visually recognize the image 231 for determination when the test subject H directs the field of view to the image 231 for determination due to a luminance difference although the test subject H cannot visually recognize the image 231 for determination itself. Consequently, the visual function detection apparatus 100 can appropriately evaluate the visual function.

The display controller 216 displays a plurality of types of the images 231 for determination different from each other in contrast at different timings, and the visual function detector 220 detects the visual function of the test subject H based on the positional relation for each of the types of the images 231 for determination. The visual function detection apparatus 100 performs an examination for each of the types of the images 231 for determination different from each other in contrast and can thus evaluate the visual function step by step.

The visual function detector 220 detects the visual function of the test subject H based on whether the position of the gazing point is present within the display region 101T. The visual function detection apparatus 100 thus performs detection of the visual function and can thus evaluate the visual function with high accuracy.

The gazing point detector 214 detects the gazing point a plurality of times while the image 231 for determination is displayed. The visual function detector 220 determines that the test subject H can visually recognize the image 231 for determination when the number of times the position of the gazing point is present within the display region 101T is equal to or more than a threshold set in advance. The visual function detection apparatus 100 thus performs detection of the visual function and can thus evaluate the visual function with high accuracy.

Figure 31:
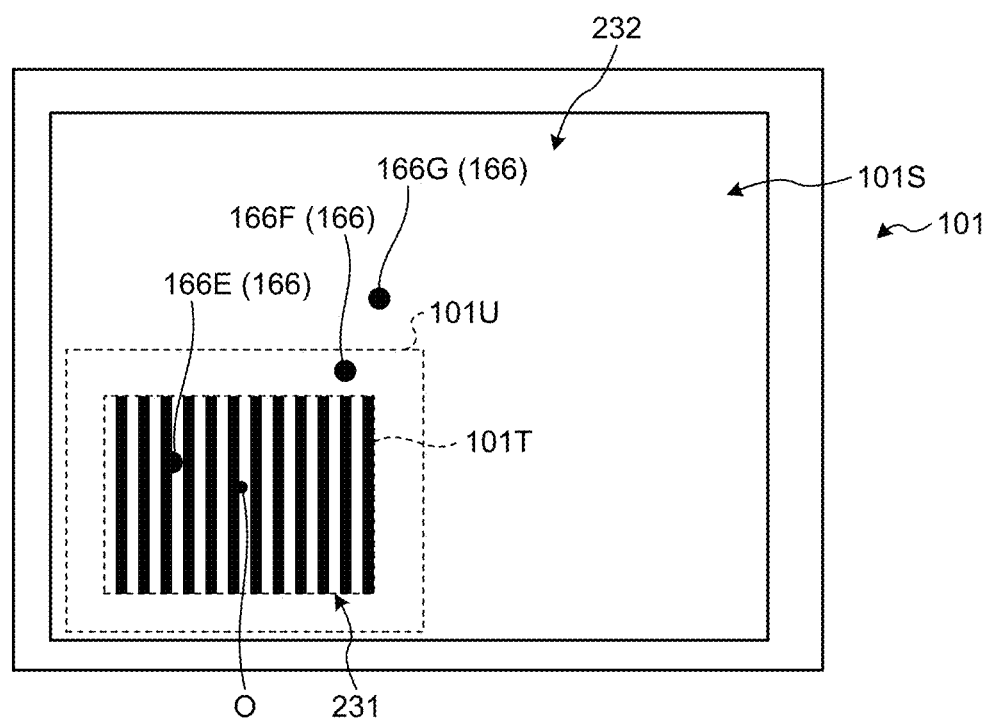
FIG. 31 is a diagram illustrating another example of detection of the effective gazing points.

FIG. 31 is diagram illustrating another example of detection of the effective gazing points. In the present embodiment, determination about whether the visual function of the test subject H satisfies the examination criterion is performed based on whether the number of the effective gazing points is equal to or more than the threshold. As to the effective gazing points, the gazing points present within the display region 101T are detected as the effective gazing points. However, the method of detecting the effective gazing points is not limited to this example. As illustrated in FIG. 31, for example, the positional relation detector 218 may also detect the gazing point present within an effective region 101U as the effective gazing points. The effective region 101U is a region on the display screen 101S overlapping with the entire region of the display region 101T and is a region larger in area than the display region 101T. In the example in FIG. 31, the gazing point 166E is the gazing point 166 present within the display region 101T, whereas the gazing point 166F is the gazing point present outside the display region 101T and within the effective region 101U. The gazing point 166G is the gazing point present outside the effective region 101U. In this case, the positional relation detector 218 defines the gazing point 166E and the gazing point 166F as the effective gazing points and does not define the gazing point 166G as the effective gazing points. Thus, detection of the visual function can appropriately be performed also when the test subject H visually recognizes the image 231 for determination simply with a slightly deviated point of view.

The effective region 101U in this case is determined to be larger in area by a certain amount than the display region 101T. This certain amount can be set to any amount. The effective region 101U may be set based on a distance from a point O of the display region 101T.

The visual function detector 220 may perform weighting on the effective gazing points. That is, when determining that the visual function of the test subject H satisfies the examination criterion, the visual function detector 220 may set the weight of the gazing point 166F to be smaller than that of the gazing point 166E. Weighting is thus performed, whereby detection of the visual function can be performed more appropriately. The visual function detector 220 may calculate a value obtained by multiplying the total number of the gazing point 166F by the coefficient k1 that is smaller than 1 and define a value obtained by adding the total number of the gazing point 166E to the value as the number of the effective gazing points, for example. Conversely, the visual function detector 220 may calculate a value obtained by multiplying the total number of the gazing point 166E by the coefficient k2 that is smaller than 1, and define a value obtained by adding the total number of the gazing point 166F to the value as the number of the effective gazing points. Further, both these coefficients k1 and k2 may be used.

The visual function detector 220 may perform weighting such that the weight of the effective gazing point detected as the gazing point 166 at an earlier timing is larger. The visual function detector 220 may multiply the total number of the effective gazing points detected as the gazing point 166 at an earlier timing than a certain time by the coefficient k2 that is larger than 1, multiply the total number of the effective gazing points detected as the gazing point 166 at a later timing than the certain time by the coefficient k1 that is smaller than 1, or combine them with each other, for example. The effective gazing point at a later timing may be given a smaller value of the coefficient to be multiplied. Even when gazing at the image 231 for determination at a timing when it is displayed, the test subject H may then move the line of sight. In such a case, the weight of the effective gazing point at an earlier timing is made larger, whereby even when the test subject H can visually recognize the image 231 for determination but then moves the line of sight, determination that the test subject H can visually recognize the image 231 for determination can be performed more favorably.

The visual function detector 220 may perform weighting such that the weight of the effective gazing point detected as the gazing point 166 at an earlier timing is smaller. That is, in a period shortly after the image 231 for determination is displayed, there may be a possibility that the reaction of the test subject H delays. Thus, with the weighting, determination that the test subject H can visually recognize the image 231 for determination can be performed more favorably. Such a way of temporal weighting can be set as appropriate in accordance with a situation.

Figure 32:
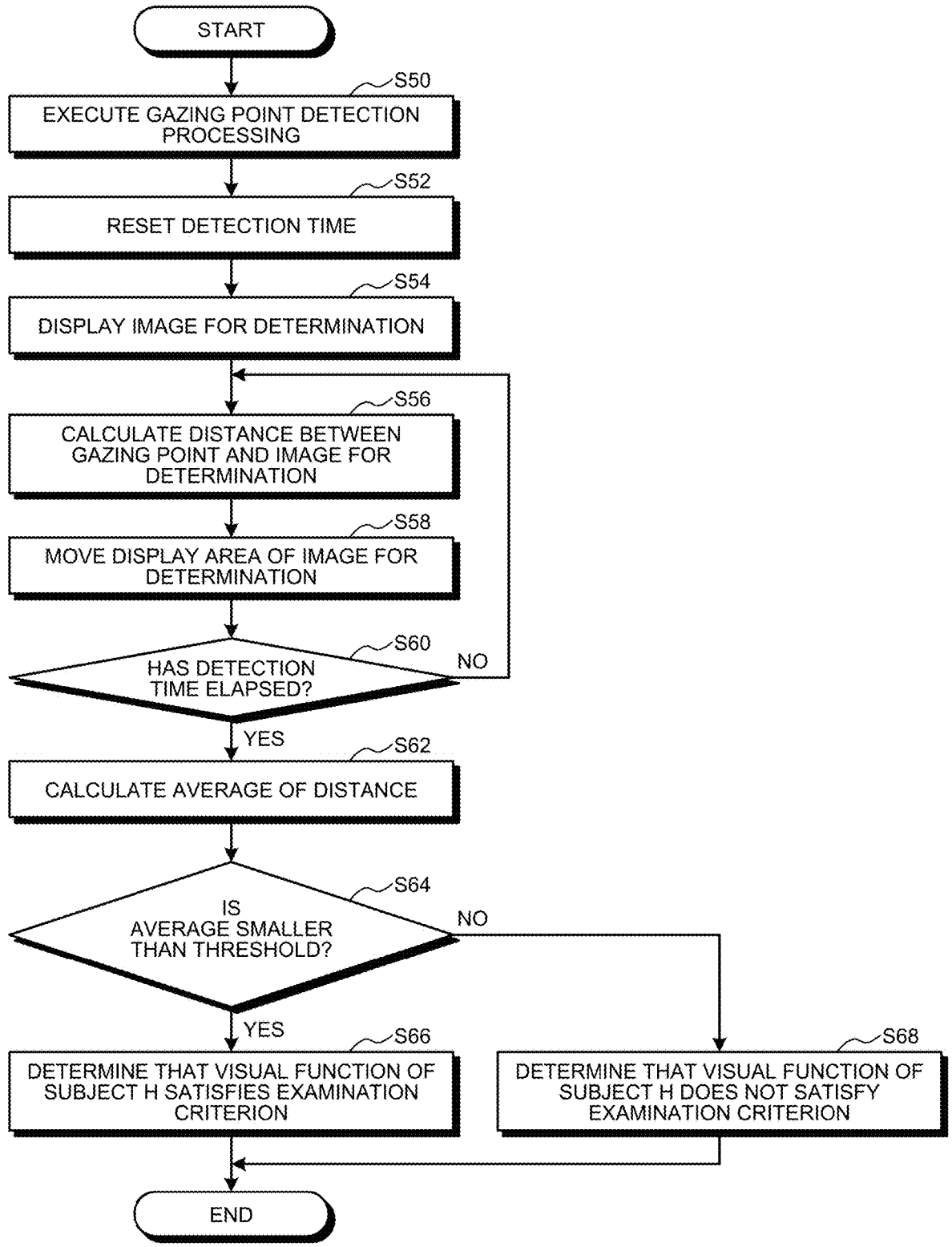
FIG. 32 is a flowchart of examining the trackability of a line of sight.
Figure 33:
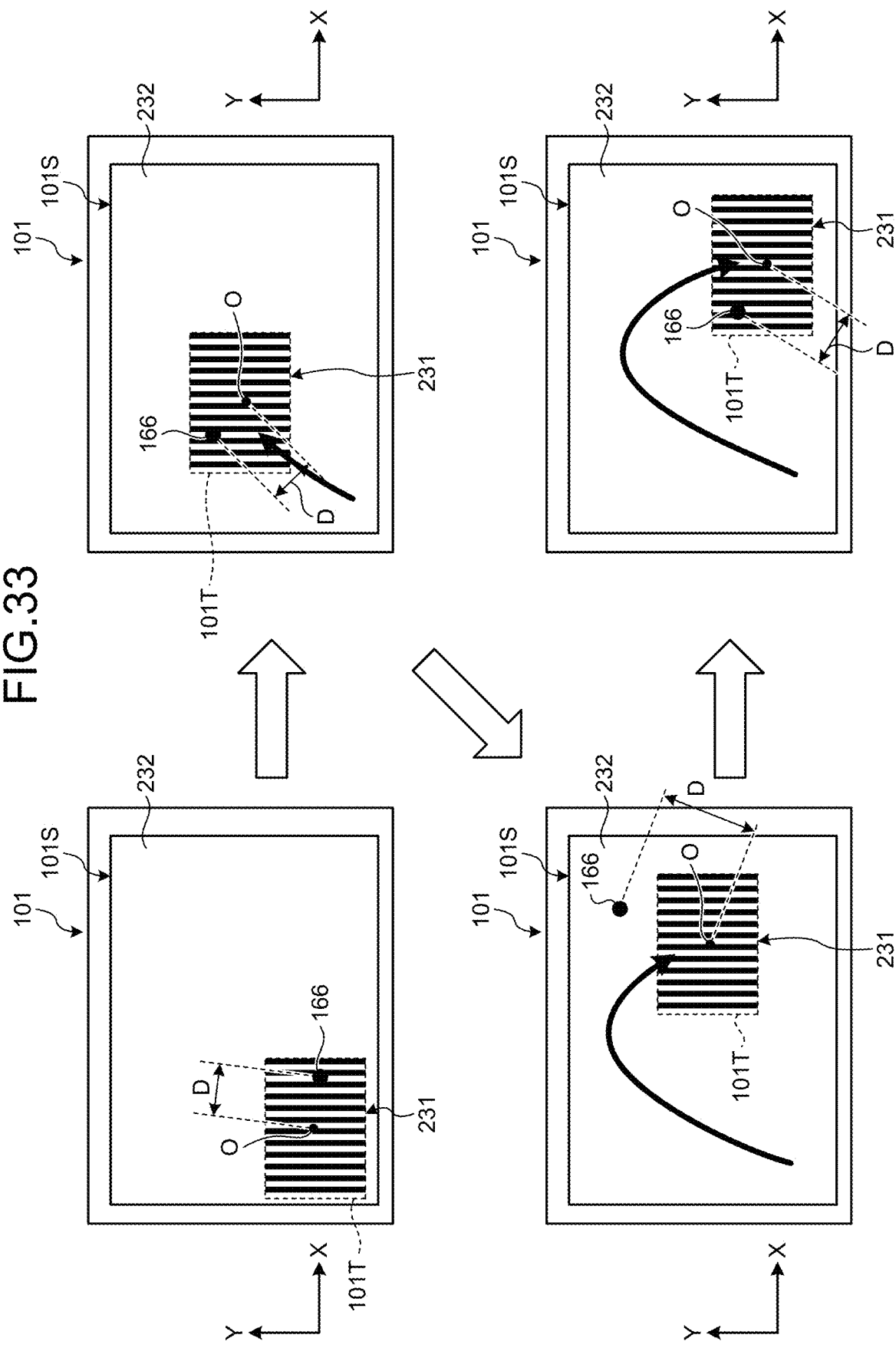
FIG. 33 is a diagram illustrating a case in which the trackability of the line of sight is examined.

The visual function detection apparatus 100 according to the present embodiment performs a test by changing a moving speed of the display region 101T, and thus can also examine the trackability of the line of sight to a moving object to be seen as the visual function. FIG. 32 is a flowchart of examining the trackability of the line of sight. FIG. 33 is a diagram illustrating a case in which the trackability of the line of sight is examined. When performing an examination of the trackability of the line of sight, the visual function detection apparatus 100 selects the image 231 for determination that can be visually recognized by the test subject H as the image 231 for determination to be displayed. That is, when the eyesight of the test subject H is determined to be the second eyesight value in FIG. 28, for example, the second image for determination (the image 231B for determination) or the first image for determination (the image 231A for determination) is used as the image 231 for determination.

As illustrated in FIG. 32, the visual function detection apparatus 100 executes the gazing point detection processing described above by the gazing point detector 214 (Step S50) to start detection of the position of the gazing point 166 of the test subject H. The visual function detection apparatus 100 then resets the detection time (Step S52) and displays the image 231 for determination by the display controller 216 (Step S54). The visual function detection apparatus 100 then calculates a distance D between the gazing point 166 and the image 231 for determination as the positional information from the position data of the gazing point 166 detected by the gazing point detector 214 and the position data of the images 231 for determination (the display region 101T) on the display screen 101S by the positional relation detector 218 (Step S56).

As illustrated in FIG. 33, the positional relation detector 218 detects a distance between the point O within the image 231 for determination (the display region 101T) and the gazing point 166 as the distance D, for example. The positional relation detector 218 calculates a distance between the point O of the image 231 for determination displayed at a timing when the gazing point 166 is detected and the gazing point 166 as the distance D. The point O is the central point of the display region 101T and may be any position so long as it is a point within the display region 101T. However, the point O preferably has a relative position within the display region 101T that does not change even when the display region 101T moves.

Referring back to FIG. 32, upon calculation of the distance D, the visual function detection apparatus 100 moves the display region 101T of the image 231 for determination (Step S58) and determines whether the detection time has elapsed (Step S60) and, if the detection time has not elapsed (No at Step S60), returns to Step S56 to calculate the distance D at a destination. That is, the processing performed until the detection time elapses in this processing is the same as the processing in FIG. 24 concerning other than detection of the distance D in place of the effective gazing points.

That is, as illustrated in FIG. 33, the visual function detection apparatus 100 gradually moves the display region 101T along the trajectory C for each frame. The moving speed of the display region 101T depends on the frame rate and a moved distance of the display region 101T for each frame. Consequently, it can be said that the visual function detection apparatus 100 moves the display region 101T such that the moving speed of the display region 101T is a certain speed. The certain speed in this example is about 100 pixels/second or more and 400 pixels/second or less, for example. However, the certain speed is not limited thereto, and can be set to any speed.

Thus, the visual function detection apparatus 100 performs detection of the gazing point 166 while continuously moving the display region 101T by leaving the image 231 for determination displayed until the detection time expires. The visual function detection apparatus 100 performs detection of the distance D until the detection time expires.

Upon a lapse of the detection time, the visual function detection apparatus 100 performs determination of the visual function of the test subject H based on the positional relation, i.e., the distance D by the visual function detector 220. Specifically, if the detection time elapses (Yes at Step S60), the visual function detector 220 calculates an average of the detected distance D (Step S62). The visual function detector 220 totals all the detected distances D and divides the total by the detected number to calculate an average, for example. The visual function detector 220 determines whether the average is smaller than a tracking threshold set in advance (Step S64). When the average is smaller than the tracking threshold (Yes at Step S64), the visual function detector 220 determines that the visual function of the test subject H satisfies the examination criterion, i.e., satisfies a trackability criterion for the moving speed at which the present examination has been performed (Step S66). When the average is not smaller than the threshold (No at Step S64), i.e., equal to or more than the threshold, the visual function detector 220 determines that the visual function of the test subject H does not satisfy the examination criterion, i.e., does not satisfy the trackability criterion for the moving speed at which the present examination has been performed (Step S68). With Step S66 or S68, the processing ends. The visual function detector 220 derives this determination result about whether the visual function of the test subject H satisfies the examination criterion as information as a criterion for detecting eyesight as the visual function and stores the information in the storage unit 222, for example.

While in the present description, the determination is performed by the comparison between the average and the threshold, the determination is not limited thereto. The visual function detection apparatus 100 may perform the determination by comparing a total value of all the detected distances D and the threshold with each other, for example. That is, the visual function detection apparatus 100 may calculate the distance D for each timing, and determine whether the gazing point 166 is moving while tracking the image 231 for determination based on the value of the calculated distance D. In this case, with a larger value of the calculated distance D, it is determined that the gazing point 166 is less likely to track the image 231 for determination, whereas with a smaller value of the calculated distance D, it is determined that the gazing point 166 is more likely to track the image 231 for determination.

The visual function detection apparatus 100 can thus detect the trackability of the line of sight based on the distance D for each timing. In this case, the visual function detection apparatus 100 performs examinations by changing the moving speed of the display region 101T, and thereby enables step-by-step examinations like eyesight. That is, the visual function detection apparatus 100 may perform the examination illustrated in FIG. 32 at a first moving speed (100 pixels/second, for example), the examination illustrated in FIG. 32 at a second moving speed (200 pixels/second, for example), and the examination illustrated in FIG. 32 at a third moving speed (400 pixels/second, for example). In this case, the visual function detection apparatus 100, if determining that the visual function of the test subject H satisfies the examination criterion after performing the examination illustrated in FIG. 32 at the first moving speed, may perform the same examination at the second moving speed. Then if determining that the visual function of the test subject H satisfies the examination criterion, the visual function detection apparatus 100 may perform the same examination at the third moving speed, for example. The second moving speed is higher than the first moving speed, and the third moving speed is higher than the second moving speed. The examinations are thus performed, whereby the trackability of the line of sight for each speed can be detected step by step.

When the examinations are thus performed step by step, the moving speed may continuously be changed. That is, upon a lapse of the detection time at Step S60 in FIG. 32, the visual function detection apparatus 100 may return to Step S52, display the image 231 for determination by the moving speed changing from the next frame, and perform an examination in a similar manner. The examinations are thus continuously performed, whereby the detection time can be reduced.

As described above, the display controller 216 changes the speed at which the position of the display region 101T is moved, the positional relation detector 218 detects the positional relation for each moving speed, and the visual function detector 220 detects the trackability of the line of sight of the test subject H to the moving object to be seen based on the positional relation for each moving speed. The visual function detection apparatus 100 thus performs the examinations while changing the moving speed and can thereby appropriately examine the trackability of the line of sight for each speed.

Figure 34:
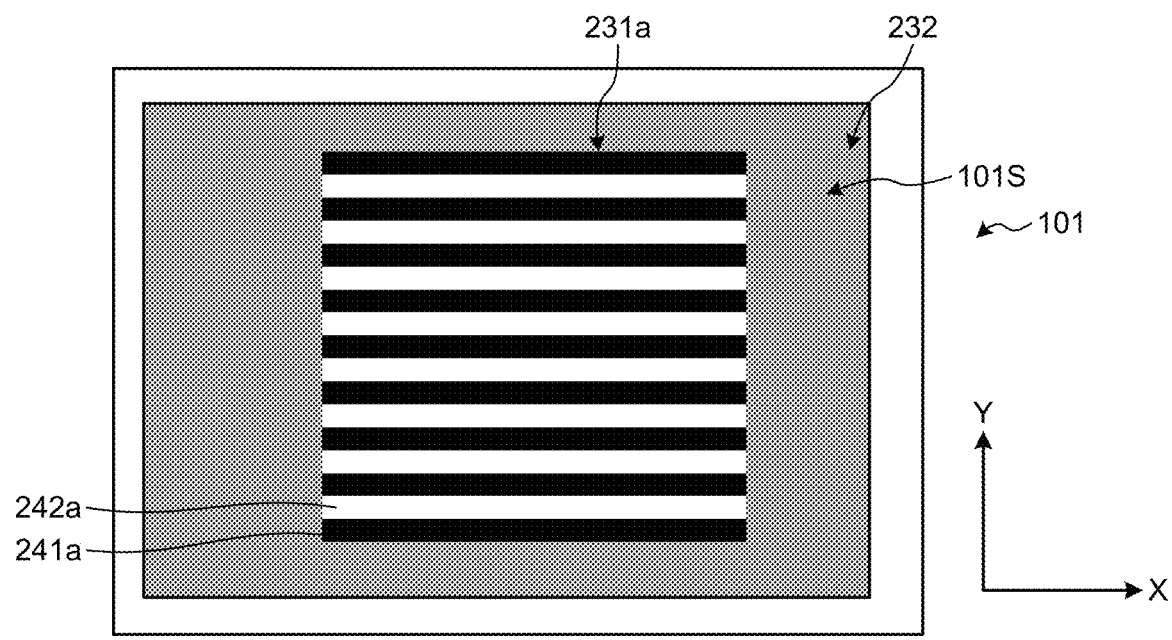
FIG. 34 is a diagram illustrating another example of the image for determination.
Figure 35:
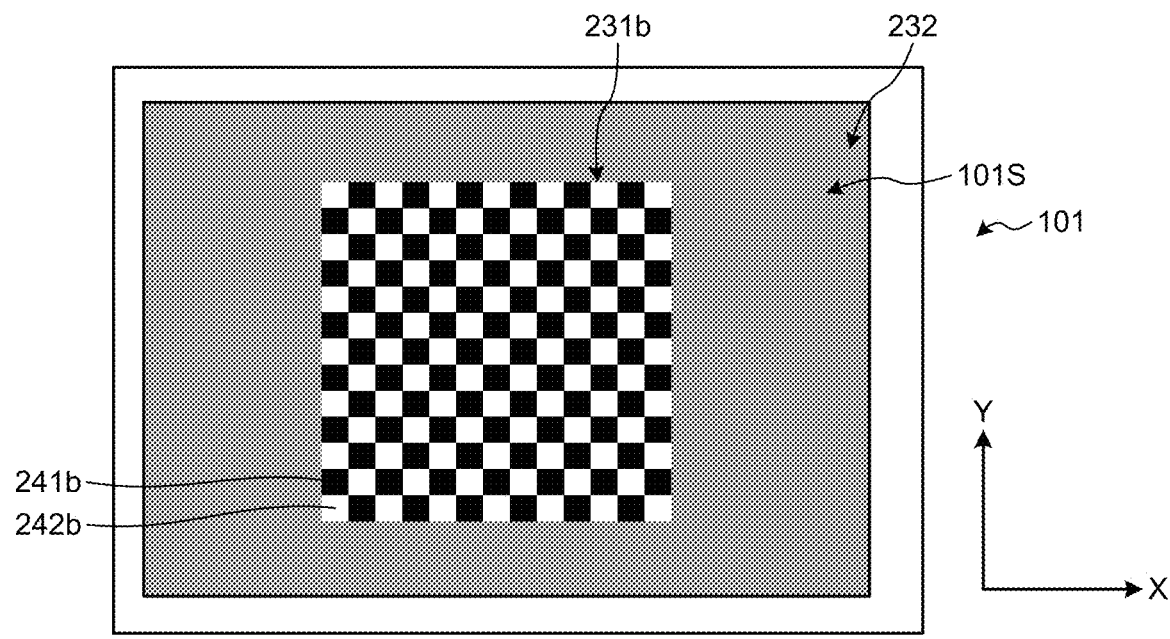
FIG. 35 is a diagram illustrating another example of the image for determination.
Figure 36:
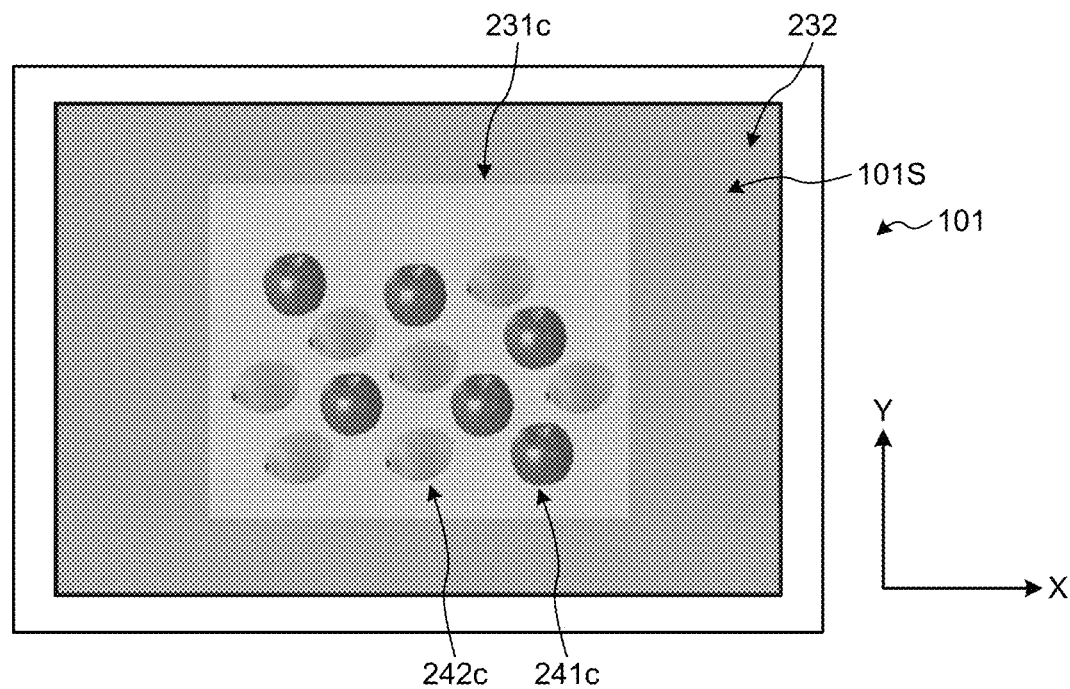
FIG. 36 is a diagram illustrating another example of the image for determination.

FIG. 34 to FIG. 36 are diagrams each illustrating another example of the image for determination. While the image 231 for determination of the present embodiment has a stripe shape in which the first images 241 and the second images 242 are alternately arranged along the X-axial direction, display of the image 231 for determination is not limited to this example. As illustrated in the image 231a for determination in FIG. 34, for example, the image 231 for determination may have a stripe shape in which the first images 241a and the second images 242a are alternately arranged along the Y-axial direction. As illustrated in the image 231b for determination in FIG. 35, the image 231 for determination may have a checkered pattern in which the first images 241b and the second images 242b are alternately arranged along the X-axial direction and the Y-axial direction. As illustrated in the image 231c for determination in FIG. 36, the first images 241c and the second images 242c may be images different from each other in luminance and shape. While in the example in FIG. 36, the first images 241c and the second images 242c are fruits, the images are not limited to fruits.

While the embodiments of the present invention have been described, the details of these embodiments do not limit the embodiments. The components described above include ones that those skilled in the art can easily think of, substantially the same ones, and ones within what is called equivalents. Further, the components described above can be combined with each other as appropriate. Further, various omissions, replacements, or modifications of the components can be made within the scope not departing from the gist of the embodiments described above.

What is claimed is:

1. A visual function detection apparatus comprising:
a display controller configured to cause an image for determination to be displayed on a display screen of a display unit;
a gazing point detector configured to detect a position of a gazing point of a test subject observing the display screen;
a positional relation detector configured to detect a distance between any position within the image for determination on the display screen and the position of the gazing point; and
a visual function detector configured to perform determination of a trackability of the line of sight of the test subject based on the distance, wherein
the display controller is further configured to move a position of the image for determination in the display screen continuously and change the moving speed of the image for determination, the positional relation detector is further configured to detect the distance for each moving speed, and the visual function detector is further configured to perform determination of the trackability of the line of sight of the test subject for each moving speed based on the distance.

2. The visual function detection apparatus according to claim 1, wherein the visual function detector is further configured to calculate an average of the detected distance for each moving speed, to determine whether the average is smaller than a tracking threshold set in advance, and to determine that the trackability of the line of sight of the test subject satisfies a trackability criterion for the moving speed if the average is smaller than the tracking threshold.

3. The visual function detection apparatus according to claim 1, wherein the display controller is further configured to move the position of the image for determination in the display screen continuously at a second moving speed which is higher than a first moving speed, if the visual function detector determines that the trackability of the line of sight of the test subject satisfies the trackability criterion after performing the examination at the first moving speed.

4. The visual function detection apparatus according to claim 1, wherein the display controller is further configured to cause a plurality of types of the images for determination with different contrasts to be displayed at different timings, and the visual function detector is configured to detect the trackability of the line of sight of the test subject based on the distance for each of the types of the images for determination.

5. A method of detecting a visual function, the method comprising:

performing display control to cause an image for determination to be displayed on a display screen of a display unit;

performing gazing point detection to detect a position of a gazing point of a test subject observing the display screen;

performing positional relation detection to detect a distance between any position within a display region of the image for determination on the display screen and the position of the gazing point;

performing visual function detection to perform determination of a trackability of the line of sight of the test subject based on the distance;

performing movement of a position of the image for determination in the display screen continuously and change of the moving speed of the image for determination at performing display control;

performing detection of the distance for each moving speed at performing positional relation detection; and performing determination of the trackability of the line of sight of the test subject for each moving speed based on the distance at performing visual function detection.

6. A non-transitory computer-readable storage medium storing a program causing a computer to execute a method, the method comprising:

display control to cause an image for determination to be displayed on a display screen of a display unit;

gazing point detection to detect a position of a gazing point of a test subject observing the display screen;

positional relation detection to detect a distance between any position within a display region of the image for determination on the display screen and the position of the gazing point;

visual function detection to perform determination of a trackability of the line of sight of the test subject based on the distance;

movement of a position of the image for determination in the display screen continuously and change of the moving speed of the image for determination at the display control;

detection of the distance for each moving speed at the positional relation detection; and determination of the trackability of the line of sight of the test subject for each moving speed based on the distance at the visual function detection.

* * * * *